US012740515B2

(12) United States Patent
Ren

(10) Patent No.: US 12,740,515 B2
(45) Date of Patent: Sep. 22, 2026

(54) CIRCULAR MOVING LAYOUT STRUCTURE AND METHOD FOR STACKED BIOLOGICAL CULTURE TRAYS ON GROUND, AND PASTURE PLANT

(71) Applicant: Qingdao Renjinli Innovation Technology Center (Sole Proprietorship), Qingdao City (CN)

(72) Inventor: Jinli Ren, Yinchuan City (CN)

(73) Assignee: Qingdao Renjinli Innovation Technology Center (Sole Proprietorship), Qingdao City (CN)

( * ) Notice: Subject to any disclaimer, the term of this patent is extended or adjusted under 35 U.S.C. 154(b) by 0 days.

(21) Appl. No.: 19/223,015

(22) Filed: May 29, 2025

(65) Prior Publication Data

US 2025/0287881 A1 Sep. 18, 2025

(30) Foreign Application Priority Data

Apr. 23, 2025 (CN) ........................ 202510518086.5

(51) Int. Cl.

| | |
|---|---|
| ***A01G 9/02*** | (2018.01) |
| ***A01G 18/62*** | (2018.01) |
| ***A01G 33/00*** | (2006.01) |
| ***A01K 67/33*** | (2025.01) |
| ***C12M 1/00*** | (2006.01) |
| ***C12M 3/00*** | (2006.01) |
| *A01K 67/362* | (2025.01) |

(52) U.S. Cl.

CPC ............. *A01G 9/023* (2013.01); *C12M 21/02* (2013.01); *C12M 23/44* (2013.01); *C12M 23/52* (2013.01); *A01G 18/62* (2018.02); *A01G 33/00* (2013.01); *A01K 67/33* (2025.01); *A01K 67/362* (2025.01)

(58) Field of Classification Search

CPC ........ A01G 18/62; A01G 33/00; A01G 9/023; A01K 67/33; A01K 67/362; C12M 21/02; C12M 23/44; C12M 23/50; C12M 23/52; Y02P 60/21

See application file for complete search history.

(56) References Cited

U.S. PATENT DOCUMENTS

| | | | | |
|---|---|---|---|---|
| 12,194,626 B2 * | 1/2025 | Cunrath | ................. | A01N 1/142 |
| 12,492,074 B2 * | 12/2025 | Jarvis | ................... | B65G 1/1373 |
| 2012/0283867 A1 * | 11/2012 | Gelbman | ............... | G01N 35/04 700/214 |

(Continued)

*Primary Examiner* — Tyler J Lee
(74) *Attorney, Agent, or Firm* — JEEN IP LAW, LLC

(57) ABSTRACT

The circular moving layout structure, method for the stacked biological culture tray, and a pasture plant are provided, the circular moving layout structure includes display areas, a waiting transfer area and an operation area, wherein each of the display areas includes multiple tray array areas, the tray array area includes multiple tray body areas, and multiple tray body areas are arranged in a single row along a first direction, and one of stacked biological culture tray bodies is correspondingly placed in each of the tray body areas in each of the tray array areas, and the stacked biological culture tray bodies are used for cultivating preset organisms, vertical projection areas of each of stacked biological culture tray bodies in each of the tray array areas on a ground are connected in a rectangular outline, each of the tray array areas is rectangular with long sides in the first direction.

9 Claims, 13 Drawing Sheets

(56) References Cited

U.S. PATENT DOCUMENTS

| | | | | |
|---|---|---|---|---|
| 2016/0137961 | A2* | 5/2016 | Clark | C12M 21/08 435/304.2 |
| 2018/0054986 | A1* | 3/2018 | Fu | A01G 31/04 |
| 2018/0139915 | A1* | 5/2018 | Au | A01G 9/045 |
| 2018/0202908 | A1* | 7/2018 | Croquette | G01N 1/42 |
| 2024/0131689 | A1* | 4/2024 | Cunrath | A01N 1/142 |
| 2024/0227168 | A9* | 7/2024 | Cunrath | A01N 1/142 |

* cited by examiner

CIRCULAR MOVING LAYOUT STRUCTURE AND METHOD FOR STACKED BIOLOGICAL CULTURE TRAYS ON GROUND, AND PASTURE PLANT

CROSS-REFERENCE TO RELATED APPLICATIONS

This application claims priority of Chinese Patent Application No. 2025105180865, filed on Apr. 23, 2025, the content of which is hereby incorporated by reference.

TECHNICAL FIELD

The disclosure relates to the technical field of biological multilayer stereoscopic culture, and in particular to a circular moving layout structure and method for stacked biological culture trays on a ground, and a pasture plant.

BACKGROUND

Biological multilayer stereoscopic culture (such as plant factory) is carried out indoors in expensive buildings, and the artificial environment of biological culture needs energy consumption to maintain, so the operating cost of biological stereoscopic culture is very high, which can be said to be an inch of land for the indoor space used for biological stereoscopic culture.

At present, the biological multilayer stereoscopic culture adopts the culture mode of shelf structure, and the basic feature of the shelf structure is supported by fixed columns, and the columns are fixedly connected with the ground, which leads to the fact that the whole biological culture device is limited by the position of the columns and cannot be free from the columns. In this case, the seeding and harvesting of biological species can only be carried out by the movable seeding device and harvesting device on the immovable shelf structure, and correspondingly, it is necessary to reserve an aisle and space for the movement of the seeding device and harvesting device beside the shelf structure. For this reason, the shelf structures need to be spaced apart and arranged in rows, so that the seeding device and harvesting device can pass through in a straight line. The problem of this shelf structure is that the aisles and spaces between the shelf structures in each row are wasted in vain.

SUMMARY

The purpose of the disclosure is to provide a circular moving layout structure and method for stacked biological culture trays on a ground, and a pasture plant, and to solve the above problems existing in the prior art.

In order to solve the above technical problems, the disclosure adopts the following technical scheme:

a circular moving layout structure of stacked biological culture trays on a ground is provided, and includes display areas, a waiting transfer area and an operation area, where each of the display areas includes multiple tray array areas, each of the tray array areas includes multiple tray body areas, and multiple tray body areas are arranged in a single row along a first direction, and one of stacked biological culture tray bodies is correspondingly placed in each of the tray body areas in each of the tray array areas, a stacked biological culture tray body is overlapped with multiple layers of biological culture trays from bottom to top, and the stacked biological culture tray bodies are used for cultivating preset organisms, which are cultured in each layer of biological culture tray, and the preset organisms may be mushrooms, plants, insects, earthworms, algae and the like, and the disclosure is not limited, the planar shape of the stacked biological culture tray body is not limited, and it may be rectangular or circular, the vertical projection areas of each of stacked biological culture tray bodies in each of the tray array areas on a ground are connected in a rectangular outline, each of the tray array areas is rectangular with long sides in the first direction, and multiple the tray array areas are arranged as the display areas along a second direction, and the first direction and the second direction are vertically arranged;

the waiting transfer area includes a temporary tray array area and at least one tray reversing area, where the temporary tray array area is used for temporarily accommodating all the stacked biological culture tray bodies in at least one of the tray array areas, and the tray reversing area is used for temporarily accommodating at least one of the stacked biological culture tray bodies; in the initial state of a preset operation cycle, the tray reversing area is arranged at an end of the temporary tray array area and communicates with the temporary tray array area from one side, or, the tray reversing area is arranged in a middle of the temporary tray reversing area to divide the temporary tray array area into two sections and communicate with the temporary tray array area from two sides, the position of the tray reversing area in the waiting transfer area is dynamic, and the position of the tray reversing area in the waiting transfer area changes with the change of the preset operation state; the temporary tray array area is used in cooperation with the tray reversing area, so as to perform preset operation on each of the stacked biological culture tray bodies; vertical projection areas of all the stacked biological culture tray bodies accommodated in the waiting transfer area on the ground are connected in a rectangular outline, the waiting transfer area is rectangular with long sides in the second direction, and a length of the waiting transfer area is greater than a sum of a length of at least one of the tray array areas and a length of the tray reversing area; a long side of the waiting transfer area corresponds to a short side of each of the tray array areas in each of the display areas, a width of the waiting transfer area is greater than or equal to a maximum side length of each of the tray body areas, so as to accommodate maximum shape of each of the stacked biological culture tray bodies, the waiting transfer area is interconnected with each of the tray array areas in each of the display areas, and all the stacked biological culture tray bodies in each of the tray array areas perform barrier-free sequential circular movement between the tray array areas and the waiting transfer area in a full-in and full-out manner;

the waiting transfer area is connected with the operation area for use;

the operation area is used for arranging a reciprocating operation device of being capable of moving back and forth, the reciprocating operation device may be a single operation device for single-link operation (such as nutrient feeding device in mushroom cultivation) or a combined operation device for multiple operation links in sequence (such as mushroom product harvesting and nutrient waste removal device in mushroom cultivation), and the reciprocating operation device moves back and forth on two long sides of the waiting transfer area in the second direction; vertical projection areas of the reciprocating operation device on the ground are connected in a rectangular outline during reciprocating movement; the operation area covers the waiting transfer area; a width of the operation area is greater than a width of the waiting transfer area; a length of the operation area is greater than or equal to a length of the waiting transfer area, so that the reciprocating operation device is capable of riding across the waiting transfer area for reciprocating movement, and during reciprocating movement, preset operation is performed on the stacked biological culture tray bodies in any position of the temporary tray array area by the tray reversing area, and a barrier-free movement of the stacked biological culture tray bodies between each of the tray array areas and the waiting transfer area is not hindered, the reciprocating operation device is provided with a gantry frame, and the width and height of the gantry frame are enough for the reciprocating operation device body to ride across each of the stacked biological culture tray bodies in the temporary tray array area without obstacles for reciprocating movement and performing operation; or, the operation area is used for arranging reciprocating operation device of being capable of moving reciprocally, and the reciprocating operation device moves reciprocally along a long side of the waiting transfer area in the second direction, and vertical projection areas of the reciprocating operation device on the ground during reciprocating movement are connected in a rectangular outline, and the operation area is adjacent to the waiting transfer area, and a length of the operation area is greater than or equal to a length of the waiting transfer area, so that the reciprocating operation device is capable of moving reciprocally along a side of the waiting transfer area, and during reciprocating movement, preset operation is performed on the stacked biological culture tray bodies in any position of the temporary tray array area by the tray reversing area, and a barrier-free movement of the stacked biological culture tray bodies between the tray array areas and the waiting transfer area is not hindered; the reciprocating operation device is provided with a cantilever frame, and the arm length and height of the cantilever frame are enough to lift the performing mechanism of the reciprocating operation device, so that the reciprocating operation device may freely move and carry out operations in a preset way on the stacked biological culture disc body which is about to enter the operation in the temporary tray array area without obstacles;

one of the display areas is configured in one waiting transfer area and one operation area, and one of the display areas is arranged on one side of one long side of the waiting transfer area and the operation area; or, two the display areas are configured in one waiting transfer area and one operation area, and one of the display areas is respectively arranged on each side of two long sides of the waiting transfer area and the operation area.

When one of the waiting transfer areas and one of the operation areas is equipped with one of the display areas, and the display area is set on one side of one long side of the waiting transfer area and the operation area, the auxiliary device (biological species supply device, culture material supply device, biological transfer device and waste transfer device) that cooperates with the reciprocating operation device to perform preset operation can be set on the side of the operation area away from the display area, and the auxiliary device may be a conveyor belt or a vehicle, or a suspended cable car.

When one of the waiting transfer areas and one of the operation areas is equipped with two of the display areas, and the display area is set on each one side of two long sides of the waiting transfer area and the operation area, the auxiliary device (biological species supply device, culture material supply device, waste transfer device) and biological transfer device that cooperates with the reciprocating operation device to perform preset operation may be set at any side of the operation area, and the auxiliary device may be a vehicle, or a suspended cable car.

Further, column structures are included, each of the display areas includes multiple rows of the column structures, one or two of the tray array areas are arranged between two adjacent rows of the column structures in the first direction, and at least one side of each of the tray body areas in each of the tray array areas corresponds to one of the column structures, so that the stacked biological culture tray bodies on the tray body areas are connected with the column structures according to a preset scheme, so that the organisms cultivated by the stacked biological culture tray bodies may directly obtain resources such as energy, carbon dioxide, oxygen, moisture, nutrients and the like from the preset facilities attached to the column structures, and the waiting transfer area and the operation area are arranged between two adjacent rows of the column structures in the second direction;

or, more than three tray array areas are arranged between two adjacent rows of the column structures in the first direction, and the waiting transfer area and the operation area are arranged between two adjacent rows of the column structures in the second direction.

The spacing distance between the column structures distributed in the tray array area and the spacing distance between the column structures distributed in the waiting transfer area and the operation area are not limited.

A circular moving method for stacked biological culture trays on a ground is provided, the method adopts the circular moving layout structure of stacked biological culture trays on a ground, where each of the stacked biological culture tray bodies includes a universal wheel tray arranged at a bottom, ground suitable for the universal wheel tray to walk in a barrier-free way is arranged in each of the tray array areas along the first direction and the waiting transfer area along the second direction, the universal wheel tray is used in cooperation with the ground, and a circular moving method for the stacked biological culture trays on the ground includes:

applying force to the universal wheel tray of each of the stacked biological culture tray bodies in a preset manner when the stacked biological culture tray bodies in a preset tray array area are performed preset operation, the direction of applying force points to the waiting transfer area, so that the universal wheel tray moves in a direction of applying force, and starting from a tray body area nearest from the waiting transfer area, transferring the stacked biological culture tray bodies in the tray array areas to the temporary tray array area in the waiting transfer area one by one from near to far, until all the stacked biological culture tray bodies are transferred; at this time, the tray array area is temporarily idle;

applying force to the universal wheel tray of each of the stacked biological culture tray bodies again after preset operation device completes preset operation on the stacked biological culture tray bodies by the tray reversing area, the direction of applying force points to the tray array area, so that the universal wheel tray moves in the direction of applying force, and starting from a tray body area farthest from the waiting transfer area, transferring the stacked biological culture tray bodies in the waiting transfer area to an original tray array area one by one from far to near, until all the stacked biological culture tray bodies are transferred, at this time, the tray array area enters the working state.

Further, the tray array area and the waiting transfer area are provided with navigation signals of being mutually connected and used in cooperation, and the navigation signals are used in cooperation with carrying robots, the navigation signals and the structure of the carrying robot are not specifically limited, and the universal wheel tray is applied force by each of the carrying robots, and the circular moving method for stacked biological culture trays on a ground includes:

starting the carrying robots when preset operation is necessary to performed on the stacked biological culture tray bodies in the preset tray array area, and starting from a tray body area nearest from the waiting transfer area, lifting or semi-lifting the stacked biological culture tray bodies in the tray array areas one by one from near to far by using the carrying robots according to the navigation signals, and transferring out of the tray array areas in the first direction, and then transferring to the waiting transfer area in the second direction and sequentially placing in the temporary tray array area until all of the stacked biological culture tray bodies are transferred;

staring the carrying robots again after the preset operation device completes the preset operation on the stacked biological culture tray bodies by the tray reversing area, and starting from a tray body area farthest from the waiting transfer area, lifting or semi-lifting the stacked biological culture tray bodies in the waiting transfer area one by one from far to near by using the carrying robots according to the navigation signals, and transferring out of the tray array areas in the second direction, and then transferring to the waiting transfer area in the second direction and transferring to an original tray array area along the first direction until all of the stacked biological culture tray bodies are transferred.

Further, a first connecting mechanism and a second connecting mechanism for chain traction are arrange at intervals at a bottom of the universal wheel tray, sinking slits of being low than the ground are arranged in the tray array areas along the first direction and in the waiting transfer area along the second direction, the sinking slits are used in cooperation with universal wheels of the universal wheel tray, the universal wheel tray is capable of spanning the sinking slits, and a first chain sprocket assembly is arranged in a sinking slit of the tray array areas, the first chain sprocket assembly is provided with a first matching structure matched with the first connecting mechanism, and the first connecting mechanism and the first matching structure are capable of being connected or separated according to instructions; a second chain sprocket assembly is arranged in a sinking slit of the waiting transfer area, and the second chain sprocket assembly is provided with a second matching structure matched with the second connecting mechanism, and the second connecting mechanism and the second matching structure are capable of being connected or separated according to instructions; the circular moving method for stacked biological culture trays on a ground includes:

firstly starting the first chain sprocket assembly to drive the first matching structure to rotate in a direction of the waiting transfer area when preset operation is necessary to performed on the stacked biological culture tray bodies in the preset tray array area, first connecting the first connecting mechanism of a universal wheel tray closest to the waiting transfer area with the first matching structure in an order from near to far, and continuously rotating the first chain sprocket assembly in a direction of the waiting transfer area, until the second connecting mechanism of the universal wheel tray moves to a position corresponding to the second chain sprocket assembly in the waiting transfer area, so that the first matching structure is separated from the first connecting mechanism, starting the second chain sprocket assembly to drive the second matching structure to approach the second connecting mechanism, so that the second matching structure is connected with the second connecting mechanism, and starting the second chain sprocket assembly to drive the universal wheel tray to move to a predetermined position in the temporary tray array area, so that the second matching structure and the second connecting mechanism are separated;

and so on, until all the stacked biological culture tray bodies in the tray array areas are transferred to the temporary tray array area in the waiting transfer area one by one, the tray array area becomes an empty tray array area;

after the preset operation device completes preset operation on the stacked biological culture tray bodies by the tray reversing area, first starting the second chain sprocket assembly in an order from near to far, so that a second connecting mechanism of a universal wheel tray closest to the empty tray array area is connected with a second matching structure, and continuously rotating the second chain sprocket assembly in a direction of the empty tray array area until the first connecting mechanism of the universal wheel tray moves a position corresponding to the first chain sprocket assembly, so that the second matching structure is separated from the second connecting mechanism, then starting the first chain sprocket assembly, so that first matching structure is connected with the first connecting mechanism, and starting the first chain sprocket assembly to drive the universal wheel tray to transfer to a predetermined position in the empty tray array area, so as to separate the first matching structure from the first connecting mechanism;

and so on, until all the stacked biological culture tray bodies in the waiting transfer area are transferred to the empty tray array areas one by one.

A circular moving method for stacked biological culture trays on a ground is provided, and adopts the circular moving layout structure of stacked biological culture trays on a ground, and further includes carrying devices, where each of the stacked biological culture tray bodies includes a tray arranged at a bottom, and the circular moving method for stacked biological culture trays on a ground includes:

starting the carrying devices when preset operation is necessary to performed on the stacked biological culture tray bodies in the preset tray array area, starting from one of the tray body areas closest to the waiting transfer area, from near to far, lifting the stacked biological culture tray bodies in the tray array area one by one by using the carrying devices, and then transferring out of the tray array area in the first direction, and then transferring to the waiting transfer area in the second direction and placing in the temporary tray array area in sequence until all of the stacked biological culture tray bodies are transferred;

starting the carrying devices again after the preset operation device completes preset operation on the stacked biological culture tray bodies by the tray reversing area, and starting from one of the tray body areas farthest from the waiting transfer area, from far to near, lifting the stacked biological culture tray bodies in the waiting transfer area one by one with the carrying devices, and then transferring out of the waiting transfer area in the second direction, and then transferring to an original tray array area in the first direction until all of the stacked biological culture tray bodies are transferred.

A circular moving method for stacked biological culture trays on a ground is provided, and adopts the circular moving layout structure of stacked biological culture trays on a ground, and further includes wheel-rail carrying devices, where each of the stacked biological culture tray bodies includes a tray arranged at a bottom, and sinking narrow rails lower than the ground are arranged in the tray array areas along the first direction and in the waiting transfer area along the second direction, a sinking narrow rail in the first direction and a sinking narrow rail in the second direction are communicated with each other, and the wheel-rail carrying devices are capable of moving along the first direction and the second direction on the sinking narrow rails, the circular moving method for stacked biological culture trays on a ground includes:

starting the wheel-rail carrying devices when preset operation is necessary to perform on the stacked biological culture tray bodies in the preset tray array area, and starting from one of the tray body areas closest to the waiting transfer area, from near to far, lifting the stacked biological culture tray bodies in the tray array areas sequentially by the wheel-rail carrying devices along the sinking narrow rails, and transferring to the temporary tray area in the waiting transfer area until all of the stacked biological culture tray bodies are transferred;

starting the wheel-rail carrying devices again after the preset operation device completes preset operation on the stacked biological culture tray bodies by the tray reversing area, and starting from one of the tray body areas farthest from the waiting transfer area, from far to near, lifting the stacked biological culture trays in the waiting transfer area sequentially by the wheel-rail carrying devices along the sinking narrow rails, and transferring to an original tray array area until all of stacked biological culture tray bodies are transferred.

A circular moving method for stacked biological culture trays on a ground is provided, and adopts the circular moving layout structure of stacked biological culture trays on a ground, and further includes a reversal tray, where each of the stacked biological culture tray bodies includes a body tray and multiple biological culture trays overlapped on the body tray, and a biological culture tray located at a bottommost is detachably connected with the body tray, the reversal tray and the body tray are capable of being used interchangeably, and the tray reversing area is arranged at at least one end of the temporary tray array area in the waiting transfer area, the circular moving method for stacked biological culture trays on a ground by the reciprocating operation device includes: placing the reversal tray in the tray reversing area;

transferring all the stacked biological culture tray bodies in the preset tray array area to the temporary tray array area;

moving the reciprocating operation device to a temporary tray array area adjacent to the tray reversing area and corresponding to one of the stacked biological culture tray bodies;

starting a performing mechanism of the reciprocating operation device, sequentially performing preset operation on each of the biological culture trays in one of the stacked biological culture tray bodies from top to bottom, and sequentially placing each of biological culture trays of completing preset operation on the reversal tray in the tray reversing area from bottom to top, so that a body tray of stacked biological culture tray body of completing preset operation becomes a new reversal tray, a corresponding area becomes a new tray reversing area, and an original tray reversing area becomes a part of the temporary tray array area;

then moving the reciprocating operation device to a temporary tray array area adjacent to the new tray reversing area, and corresponding to a stacked biological culture tray body waiting for preset operation;

starting a performing mechanism of the reciprocating operation device, sequentially performing preset operation on each of biological culture trays in one of the stacked biological culture tray bodies waiting for preset operation from top to bottom, and sequentially placing each of biological culture trays of completing the preset operation on a new reversal tray on a new tray reversing area from bottom to top, so that a corresponding area becomes another new tray reversing area, and an original new tray reversing area becomes a part of the temporary tray array area;

and so on, until all stacked biological culture tray bodies waiting for preset operation in the temporary tray array area complete preset operation, a body tray of a stacked biological culture tray body of completing the preset operation finally becomes a last new reversal tray, and a corresponding area becomes a last new tray reversing area; and sequentially transferring each of the stacked biological culture tray bodies of completing preset operation in the temporary tray array area to the original tray array area.

A circular moving method for stacked biological culture trays on a ground is provided, and adopts the circular moving layout structure of stacked biological culture trays on a ground, and further includes a reversal tray, where each of the stacked biological culture tray bodies includes a body tray and multiple biological culture trays overlapped on the body tray, and a biological culture tray located at a bottommost is detachably connected with the body tray, the reversal tray and the body tray are capable of being used interchangeably, and the tray reversing area is arranged in a middle of the temporary tray array area in the waiting transfer area, and is located near the tray array area of being preset to wait for preset operation, the circular moving method for stacked biological culture trays on a ground by the reciprocating operation device includes:

firstly transferring a part of stacked biological culture tray bodies in the preset tray array area waiting for preset operation to the temporary tray array area on one side of the tray array area in the waiting transfer area, then transferring another part of stacked biological culture tray bodies in the preset tray array area to the temporary tray array area on an other side of the tray array area in the waiting transfer area, and setting the tray reversing area at a position near an intersection of the tray array area and the waiting transfer area;

placing the reversal tray in the tray reversing area;

moving the reciprocating operation device to a temporary tray array area adjacent to the tray reversing area at one side of the tray reversing area and corresponding to one of the stacked biological culture tray bodies;

starting a performing mechanism of the reciprocating operation device, sequentially performing preset operation on each of biological culture trays in one of the stacked biological culture tray bodies waiting for preset operation from top to bottom, and sequentially placing each of biological culture trays of completing preset operation on a reversal tray on a tray reversing area from bottom to top, so that the body tray of each of the stacked biological culture tray bodies of completing preset operation becomes into another new reversal tray, a corresponding area becomes another new tray reversing area, and an original tray reversing area becomes a part of the temporary tray array area;

then moving the reciprocating operation device to a temporary tray array area adjacent to the new tray reversing area, and corresponding to one of the stacked biological culture tray bodies waiting for preset operation;

starting a performing mechanism of the reciprocating operation device, sequentially performing preset operation on each of the biological culture trays in one of the stacked biological culture disc bodies waiting for preset operation from top to bottom, and sequentially placing each of the biological culture trays of completing preset operation on a new reversal tray on a new tray reversing area from bottom to top, so that the body tray of each of the stacked biological culture disc bodies of completing preset operation becomes another new reversal tray, a corresponding area becomes another new tray reversing area, and an original new tray reversing area becomes a part of the temporary tray array area;

and so on, until all the stacked biological culture tray bodies waiting for preset operation in the temporary tray array area at one side of the tray reversing area completes preset operation, one of the body tray of the stacked biological culture tray bodied of completing the preset operation finally becomes another new reversal tray, and corresponding area becomes another new tray reversing area;

sequentially transferring each of the stacked biological culture tray bodies of having completed preset operation in the temporary tray array area to an original tray array area;

transferring another new reversal tray to an opposite end of a temporary tray array area on an other side;

similarly, moving the reciprocating operation device to the temporary tray array area on the other side and corresponding to one of the stacked biological culture tray bodies adjacent to another new reversal tray;

repeating above operation flow until remaining stacked biological culture tray bodies complete preset operation and sequentially transferring to an original tray array area.

A pasture plant (specialized in producing 7-day-old barley/wheat sprouts) is provided, and adopts the circulating operation method of the stacked biological culture trays on a ground, and operates on the circulating moving layout structure of the stacked biological culture trays on a ground, and further includes a biological harvesting and transferring parking space, a biological harvesting and transferring conveyor belt, a biological species sowing and supplying conveyor belt, a biological species processing facility and a biological cultivation water supplying facility, where the biological harvesting and transferring parking space is arranged at preset ends of the waiting transfer area and the operation area in the second direction, and the biological harvesting and transferring conveyor belt is arranged corresponding to the operation area and arranged outside the operation area, and is used for receiving pasture products harvested from the stacked biological culture tray bodies by the reciprocating operation device and transferring to the biological harvesting and transferring parking space so as to be quickly loaded and transported away, where the biological species processing facility is arranged outside one side of the display area away from the biological harvesting and transferring parking space, and the biological species sowing and feeding conveyor belt is arranged corresponding to the operation area and arranged outside the operation area, the biological species sowing and supplying conveyor belt is arranged in parallel with the biological species harvesting and transferring conveyor belt and is located at one side or below the biological species harvesting and transferring conveyor belt; one end of the biological species sowing and supplying conveyor belt reaches the biological species harvesting and transferring parking space, and an other end reaches the biological species processing facility for receiving pasture seeds (such as barley seeds or wheat seeds) from biological harvesting and transferring parking space, and transferring the seeds to the biological species processing facility; and the biological cultivation water supplying facility is arranged outside one side of the display area away from the waiting transfer area, and is used for supplying the stacked biological culture trays in each of the tray array areas with water required for cultivating pasture.

Compared with the prior art, the disclosure has the following beneficial technical effects:

the circular moving layout structure, method for the stacked biological culture tray, and a pasture plant of the disclosure are provided with the display area, the waiting transfer area and the operation area, and the waiting transfer area includes the temporary tray array area and at least one tray reversing area, and through the cooperation of the temporary tray array area and the tray reversing area, various preset operations including biological species sowing and/or biological harvesting operations may be conveniently performed on each stacked biological culture tray body. Compared with the prior art, the plane utilization rate and the space utilization rate of the biological stereoscopic culture plant are greatly improved, the overall structural design is reasonable, the biological culture space can be fully utilize, the cost is effectively saved, the use is convenient, and the biological stereoscopic culture plant is suitable for popularization and application.

BRIEF DESCRIPTION OF THE DRAWINGS

In order to explain the embodiments of the disclosure or the technical scheme in the prior art more clearly, the drawings needed in the embodiments will be briefly introduced below. Obviously, the drawings in the following description are only some embodiments of the disclosure, and other drawings can be obtained by ordinary skilled in the field without creative efforts.

LIST OF REFERENCE CHARACTERS

Figure 1:
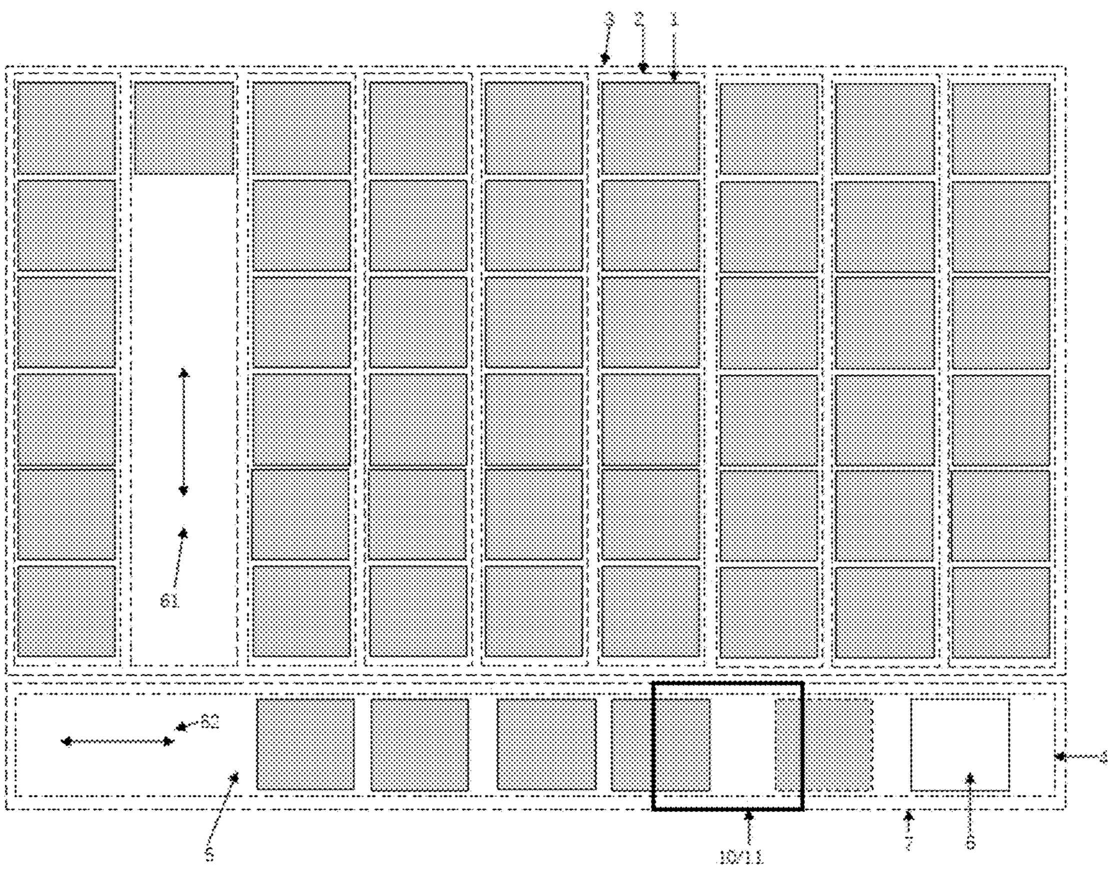
FIG. 1 is a structural schematic diagram of a circular moving layout structure of stacked biological culture trays on a ground according to embodiment 1 of the disclosure.

1 tray body area; 2 tray array area; 3 display area; 4 waiting transfer area; 5 temporary tray array area; 6 tray reversing area; 7 operation area; 8 column structure; 9 new tray reversing area; 10 reciprocating operation device; 11 gantry reciprocating operation device; 12 single-sided reciprocating operation device; 13 stacked biological culture tray body; 14 body tray; 15 reversal tray; 20 universal wheel tray; 21 tray; 22 sinking narrow rail; 23 universal wheel; 30 carrying robot; 31 carrying device; 32 wheel-rail carrying device; 33 carrying driving wheel; 40 first chain sprocket assembly; 41 first connecting mechanism; 42 first mating structure; 50 second chain sprocket assembly; 51 second connecting mechanism; 52 second mating structure; 60 direction of applying force; 61 first direction; 62 second direction; 63 navigation signal; 64 ground; 70 pasture plant; 71 access door of plant; 72 biological harvesting and conveyor belt; 73 biological species sowing and supplying conveyor belt; 74 biological harvesting and transferring parking space; 75 biological species processing facilities; 76 biological cultivation water supplying facility; 77 biological cultivation nutrient supplying facility; and 78 control area.

DETAILED DESCRIPTION OF THE EMBODIMENTS

In the following, embodiments of the disclosure will be described in detail, examples of which are illustrated in the accompanying drawings, where the same or similar reference numerals indicate the same or similar elements or elements having the same or similar functions throughout. The embodiments described below by referring to the drawings are exemplary, only for explaining the disclosure, and cannot be understood as limiting the disclosure.

In the description of the disclosure, it should be understood that the azimuth or positional relationship indicated by the terms "length", "width", "inside" and "outside" is based on the azimuth or positional relationship shown in the attached drawings, only for the convenience of describing the disclosure and simplifying the description, and does not indicate or imply that the device or element referred to must have a specific orientation, be constructed and operated in a specific orientation, so it cannot be understood as the disclosure. In addition, the terms "first" and "second" are only used for descriptive purposes, and cannot be understood as indicating or implying relative importance or implicitly indicating the number of indicated technical features. Therefore, the features defined as "first" and "second" may include one or more of these features explicitly or implicitly. In the description of the disclosure, "multiple" means two or more, unless otherwise specifically defined.

In the description of the disclosure, it should be noted that unless otherwise specified and limited, the terms "installation", "connection" and "connecting" should be broadly understood, for example, fixed connection, detachable connection or integrated connection. It also may be directly connected, indirectly connected through an intermediary, also be the internal connection of two elements or the interaction between two elements. For those skilled in the art, the specific meanings of the above terms in the disclosure may be understood according to specific situations.

The technical scheme provided by each embodiment of the disclosure will be described in detail with reference to the attached drawings.

Embodiment 1

Figure 2:
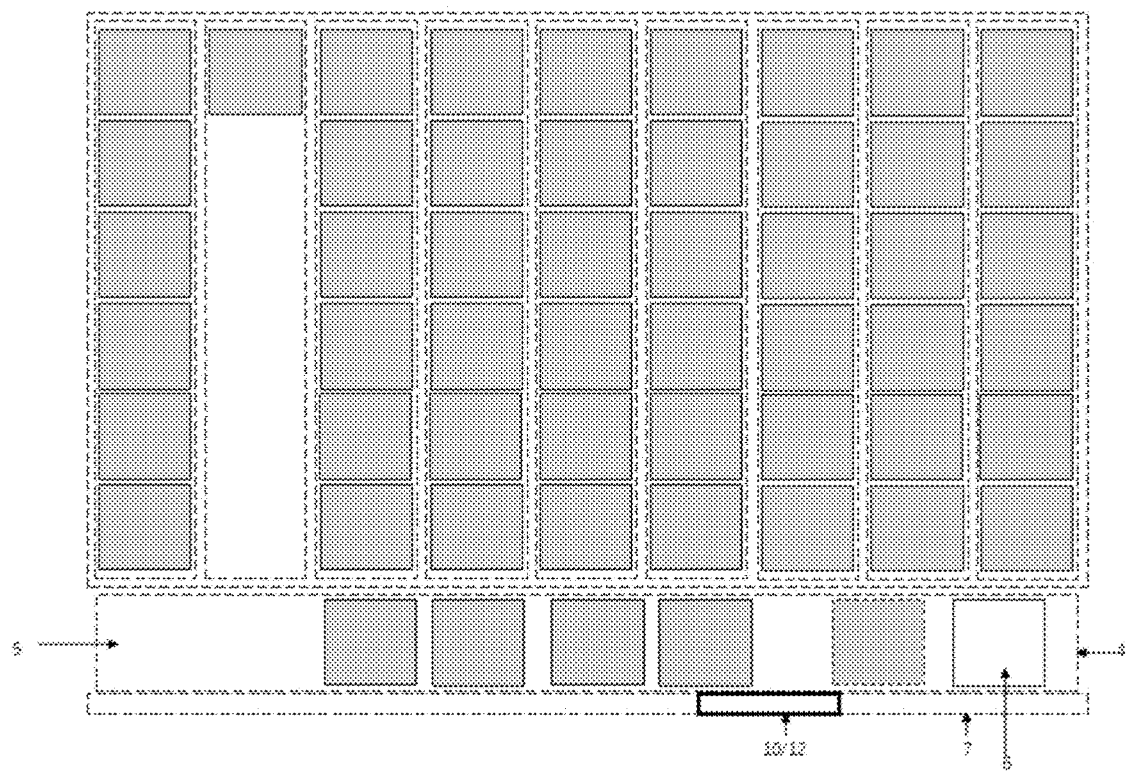
FIG. 2 is a structural schematic diagram of a circular moving layout structure of stacked biological culture trays on a ground according to embodiment 1 of the disclosure.

As shown in FIG. 1 and FIG. 2, a circular moving layout structure of stacked biological culture trays on a ground in Embodiment 1 includes a display area 3, a waiting transfer area 4 and an operation area 7. The display areas includes multiple tray array areas 2, each of the tray array areas 2 includes multiple tray body areas 1, and multiple tray body areas 1 are arranged in a single row along a first direction 61, and one of stacked biological culture tray bodies 13 is correspondingly placed in each of the tray body areas 1 in the tray array area 2, and the stacked biological culture tray bodies 13 are used for cultivating preset organisms, where, the preset organisms include plants, insects, earthworms, mushrooms, algae, etc. The vertical projection areas of each of stacked biological culture tray bodies 13 in the tray array area 2 on a ground are connected in a rectangular outline, the tray array area 2 is rectangular with long sides in the first direction 61, and multiple the tray array areas 2 are arranged as the display area 3 along a second direction 62. In the display area 3, there is no wide corridor that must be set in the prior art, which greatly improves the utilization rate of the biological stereoscopic culture space. and the first direction 61 and the second direction 62 are vertically arranged.

Where, the waiting transfer area 4 includes a temporary tray array area 5 and at least one tray reversing area 6, where the temporary tray array area 5 is used for temporarily accommodating all the stacked biological culture tray bodies 13 in at least one of the tray array areas 2, and the tray reversing area 6 is used for temporarily accommodating at least one of the stacked biological culture tray bodies 13; the tray reversing area 6 is arranged at an end of the temporary tray array area 5 and communicates with the temporary tray array area 5 from one side.

At this time, the temporary tray array area 5 is used in cooperation with the tray reversing area 6, so as to perform preset operation on each of the stacked biological culture tray bodies 13, the preset operation at least includes one of sowing biological species, harvesting biological species, adding biological culture materials, and removing waste after biological culture; vertical projection areas of all the stacked biological culture tray bodies 13 accommodated in the waiting transfer area 4 on the ground are connected in a rectangular outline, the waiting transfer area 4 is rectangular with long sides in the second direction 62, and a length of the waiting transfer area 4 is greater than a sum of a length of at least one of the tray array areas 2 and a length of the tray reversing area 6; a long side of the waiting transfer area 4 corresponds to a short side of each of the tray array areas in the display area 3, a width of the waiting transfer area 4 is greater than or equal to a maximum side length of the tray body area 1, the waiting transfer area 4 is interconnected with each of the tray array areas 2 in the display area 3, and all the stacked biological culture tray bodies 13 in each of the tray array areas 2 perform barrier-free sequential circular movement between the tray array area 2 and the waiting transfer area 4 in a full-in and full-out manner.

Further, the waiting transfer area 4 is connected with the operation area 7 for use.

where, as shown in FIG. 1, the operation area 7 is used for arranging a reciprocating operation device 10 of being capable of moving back and forth, and the reciprocating operation device 10 moves back and forth on two long sides of the waiting transfer area 4 in the second direction 62. The reciprocating operation device 10 adopts gantry reciprocating operation device 11, the reciprocating operation device 11 may be trackless movable device or rail movable device. The rail of the rail movable device is a sunken rail below the ground, so as not to hinder the movement of the stacked biological culture tray body 13 between the waiting transfer area 4 and the tray array area 2. The vertical projection areas of the reciprocating operation device 10 on the ground are connected in a rectangular outline during reciprocating movement; the operation area 7 covers the waiting transfer area 4; a width of the operation area 7 is greater than a width of the waiting transfer area 4; a length of the operation area 7 is greater than or equal to a length of the waiting transfer area 4, so that the reciprocating operation device 10 is capable of riding across the waiting transfer area 4 for reciprocating movement, and during reciprocating movement, preset operation (such as performing biological species sowing and/or biological harvesting operations) is performed on the stacked biological culture tray bodies 13 in any position of the temporary tray array area 5 by the tray reversing area 6, and a barrier-free movement of the stacked biological culture tray bodies 13 between the tray array area 2 and the waiting transfer area 4 is not hindered; or, as shown in FIG. 2, the operation area 7 is used for arranging reciprocating operation device 10 of being capable of moving reciprocally, and the reciprocating operation device 10 moves reciprocally along a long side of the waiting transfer area 4 in the second direction 62. The reciprocating operation device 10 adopts a single-sided reciprocating operation device 12, and vertical projection areas of the reciprocating operation device 10 on the ground during reciprocating movement are connected in a rectangular outline, and the operation area 7 is adjacent to the waiting transfer area 4, and a length of the operation area 7 is greater than or equal to a length of the waiting transfer area 4, so that the reciprocating operation device 10 is capable of moving reciprocally along a side of the waiting transfer area 4, and during reciprocating movement, preset operation such as biological species sowing and/or biological harvesting is performed on the stacked biological culture tray bodies 13 in any position of the temporary tray array area 5 by the tray reversing area 6, and a barrier-free movement of the stacked biological culture tray bodies between the tray array area 2 and the waiting transfer area 4 is not hindered.

In this Embodiment 1, one of the display areas 3 is configured in one waiting transfer area 4 and one operation area 7, and one of the display areas 3 is arranged on one side of one long side of the waiting transfer area 4 and the operation area 7; or, two the display areas 3 are configured in one waiting transfer area 4 and one operation area 7, and one of the display areas 3 is respectively arranged on each side of two long sides of the waiting transfer area 4 and the operation area 7.

Embodiment 2

Figure 3:
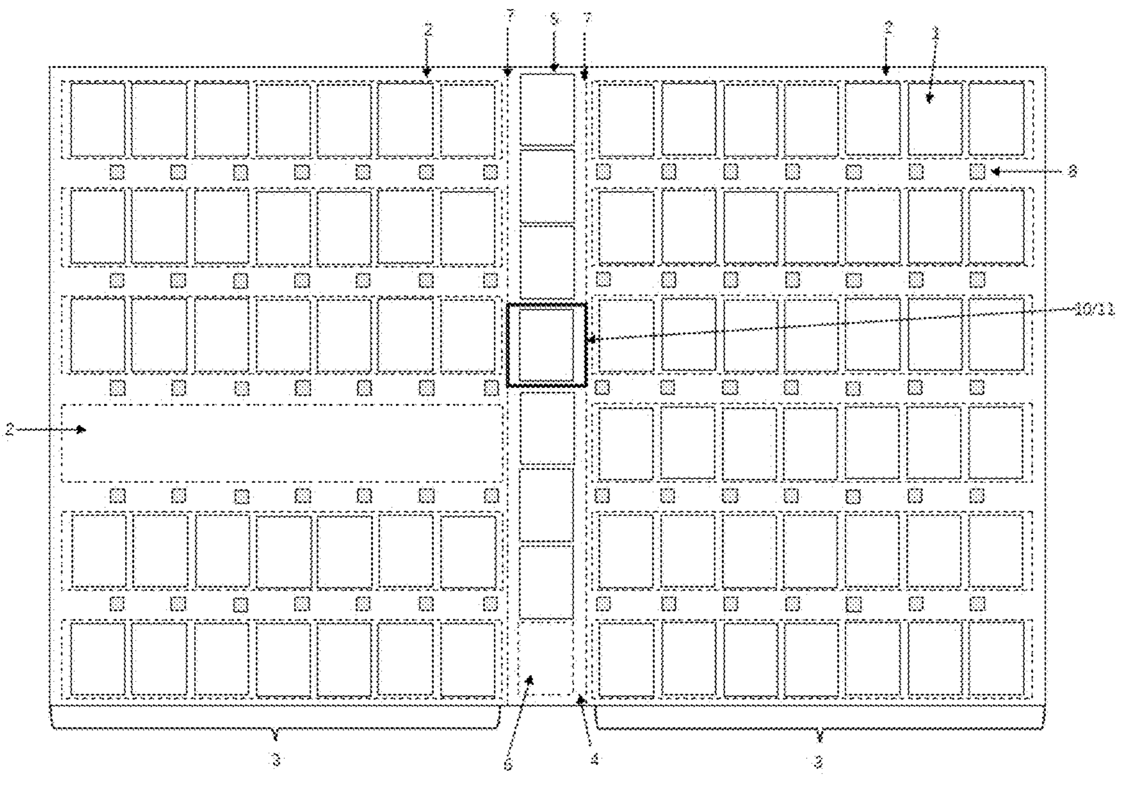
FIG. 3 is a structural schematic diagram of a circular moving layout structure of stacked biological culture trays on a ground according to embodiment 2 of the disclosure.
Figure 4:
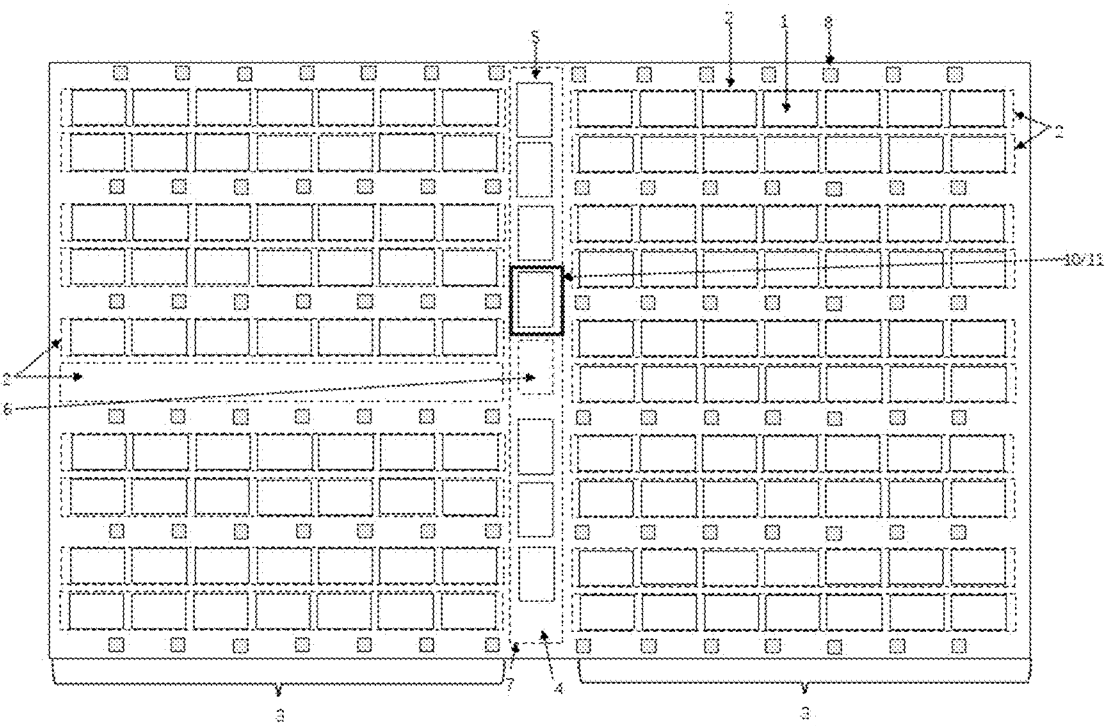
FIG. 4 is a structural schematic diagram of a circular moving layout structure of stacked biological culture trays on a ground according to embodiment 2 of the disclosure.
Figure 5:
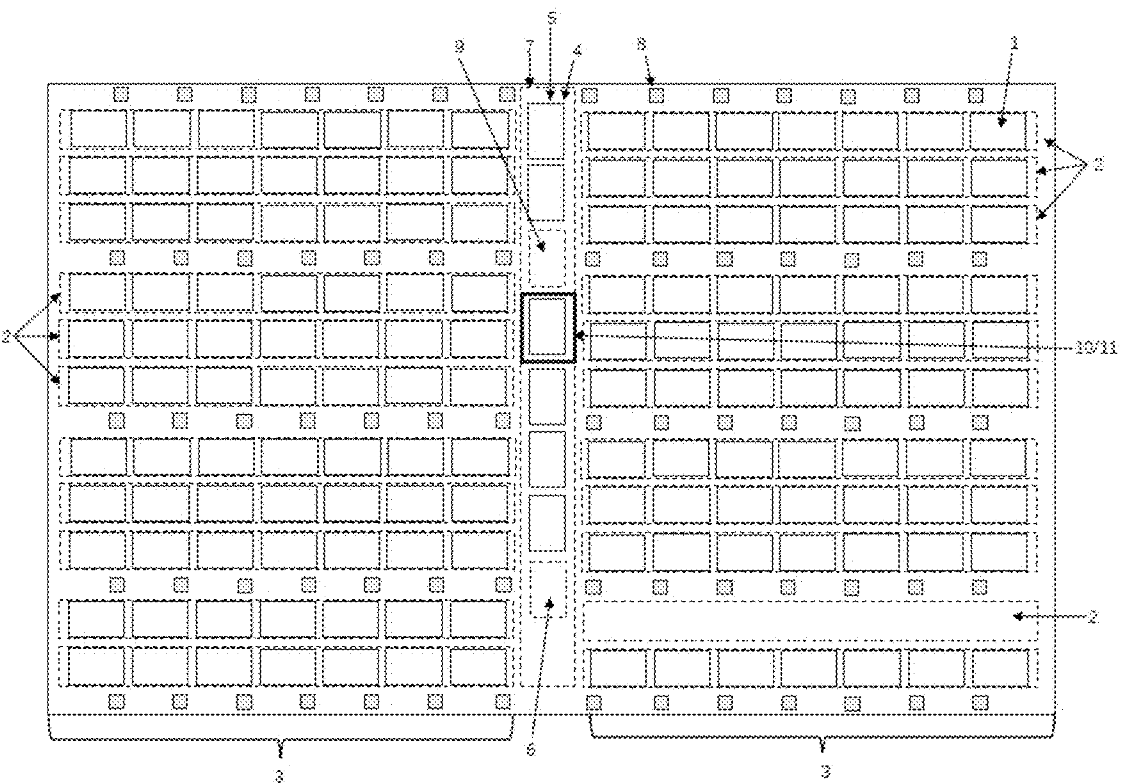
FIG. 5 is a structural schematic diagram of a circular moving layout structure of stacked biological culture trays on a ground according to embodiment 2 of the disclosure.

As shown in FIGS. 3 to 5, the difference between the circular moving layout structure of stacked biological culture trays on a ground in Embodiment 2 and Embodiment 1 is that, column structures are further included, where the display area 3 includes multiple rows of the column structures 8, as shown in FIG. 3, one tray array area 2 is arranged between two adjacent rows of column structures 8 in the first direction 61, or as shown in FIG. 4, two tray array areas 2 are arranged between two adjacent rows of column structures 8 in the first direction 61. At least one side of the tray body area 2 in the tray array area 2 corresponds to one of the column structures 8, so that the stacked biological culture tray bodies 13 on the tray body area 1 are connected with the column structures 8 according to a preset scheme, and the waiting transfer area 4 and the operation area 7 are arranged between two adjacent rows of the column structures 8 in the second direction 62.

As shown in FIG. 4, the tray reversing area 6 can also be set in the middle of the temporary tray array area 5, the temporary tray array area 5 is divided into two sections and communicated with the temporary tray array area 5 from two sides.

In this Embodiment 2, as shown in FIG. 5, more than three tray array areas 2 are arranged between two adjacent rows of the column structures 8 in the first direction 61, and the waiting transfer area 4 and the operation area 7 are arranged between two adjacent rows of the column structures 8 in the second direction 62.

Embodiment 3

Figure 6:
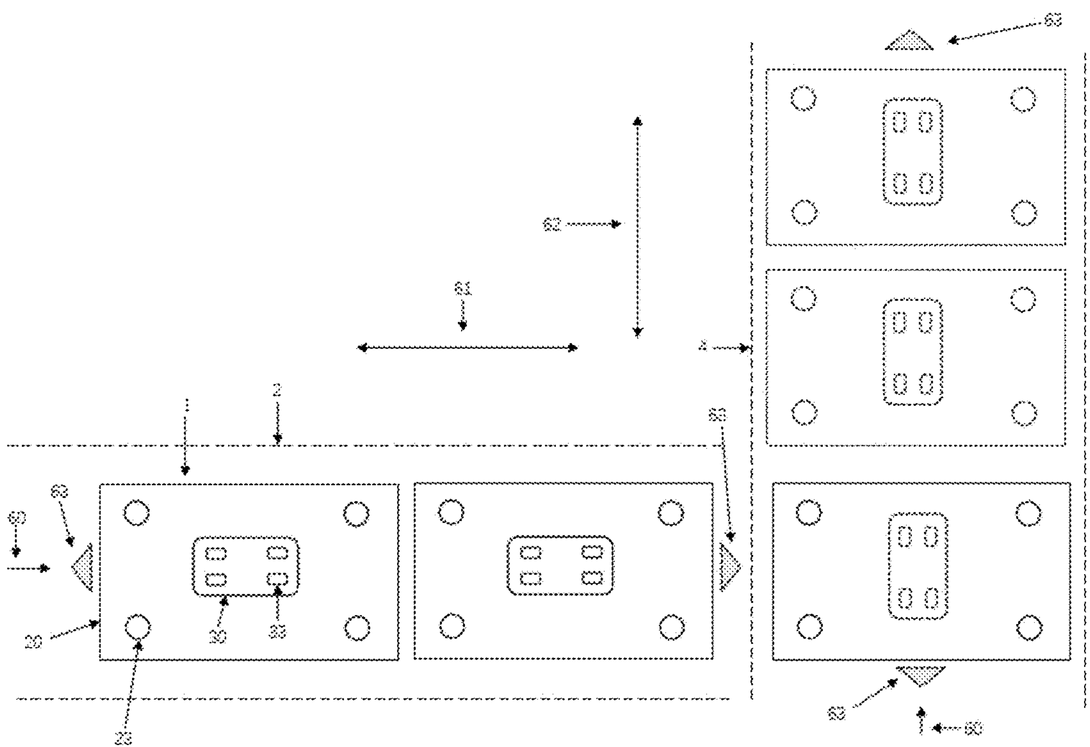
FIG. 6 is a structural schematic diagram of a circular moving layout structure of stacked biological culture trays on a ground according to embodiment 3 of the disclosure.

As shown in FIG. 6, a circular moving method for stacked biological culture trays on a ground Embodiment 3 adopts the circular moving layout structure of stacked biological culture trays on a ground, the stacked biological culture tray body 13 includes a universal wheel tray 20 arranged at a bottom, ground suitable for the universal wheel tray 20 to walk in a barrier-free way is arranged in each of the tray array area 2 along the first direction 61 and the waiting transfer area 4 along the second direction 62, the universal wheel tray 20 is used in cooperation with the ground, and a circular moving method for the stacked biological culture trays on the ground includes:

When the stacked biological culture tray bodies 13 in a preset tray array area 2 are performed preset operation (such as biological species sowing or biological harvesting operation), force is applied to the universal wheel tray 20 of the stacked biological culture tray body 13 in a preset manner, so that the universal wheel tray 20 moves in a direction of applying force 60, and it is started from a tray body area 1 nearest from the waiting transfer area 4, the stacked biological culture tray bodies 13 in the tray array area 2 are transferred to the temporary tray array area 5 in the waiting transfer area 4 one by one from near to far, until all the stacked biological culture tray bodies are transferred.

After preset operation device completes preset operation on the stacked biological culture tray bodies 13 by the tray reversing area 6, force is applied to the universal wheel tray 20 of the stacked biological culture tray bodies 13 again, so that the universal wheel tray 20 moves in the direction of applying force 60, and it is started from a tray body area 1 farthest from the waiting transfer area 4, the stacked biological culture tray bodies 13 in the waiting transfer area 4 are transferred to an original tray array area 2 one by one from far to near, until all the stacked biological culture tray bodies are transferred.

Embodiment 4

As shown in FIG. 6, the difference between the circular moving method for stacked biological culture trays on a ground in Embodiment 4 and Embodiment 3 is that, the tray array area 2 and the waiting transfer area 4 are provided with navigation signals 63 of being mutually connected and used in cooperation, and the navigation signals 63 are used in cooperation with carrying robots 30, and the universal wheel tray 20 is applied force by the carrying robots 30, and at this time, the circular moving method for stacked biological culture trays on a ground includes:

when preset operation is necessary to performed on the stacked biological culture tray bodies 13 in the preset tray array area 2, the carrying robots are started, and it is started from a tray body area 1 nearest from the waiting transfer area 4, the stacked biological culture tray bodies 13 in the tray array area 2 are lifted or semi-lifted one by one from near to far by using the carrying robots 30 according to the navigation signals 63, and transferred out of the tray array area 2 in the first direction 61, and then transferred to the waiting transfer area 4 in the second direction 62 and sequentially placed in the temporary tray array area 5 until all of the stacked biological culture tray bodies are transferred;

after the preset operation device completes the preset operation on the stacked biological culture tray bodies 13 by the tray reversing area 6, the carrying robots 30 are started again, and it is started from a tray body area 1 farthest from the waiting transfer area 4, the stacked biological culture tray bodies 13 in the waiting transfer area 4 are lifted or semi-lifted one by one from far to near by using the carrying robots 30 according to the navigation signals 63, and transferred out of the tray array area 4 in the second direction 62, and then transferred to the waiting transfer area 4 in the second direction 62 and transferred to an original tray array area 2 along the first direction 61 until all of the stacked biological culture tray bodies are transferred.

Embodiment 5

Figure 7:
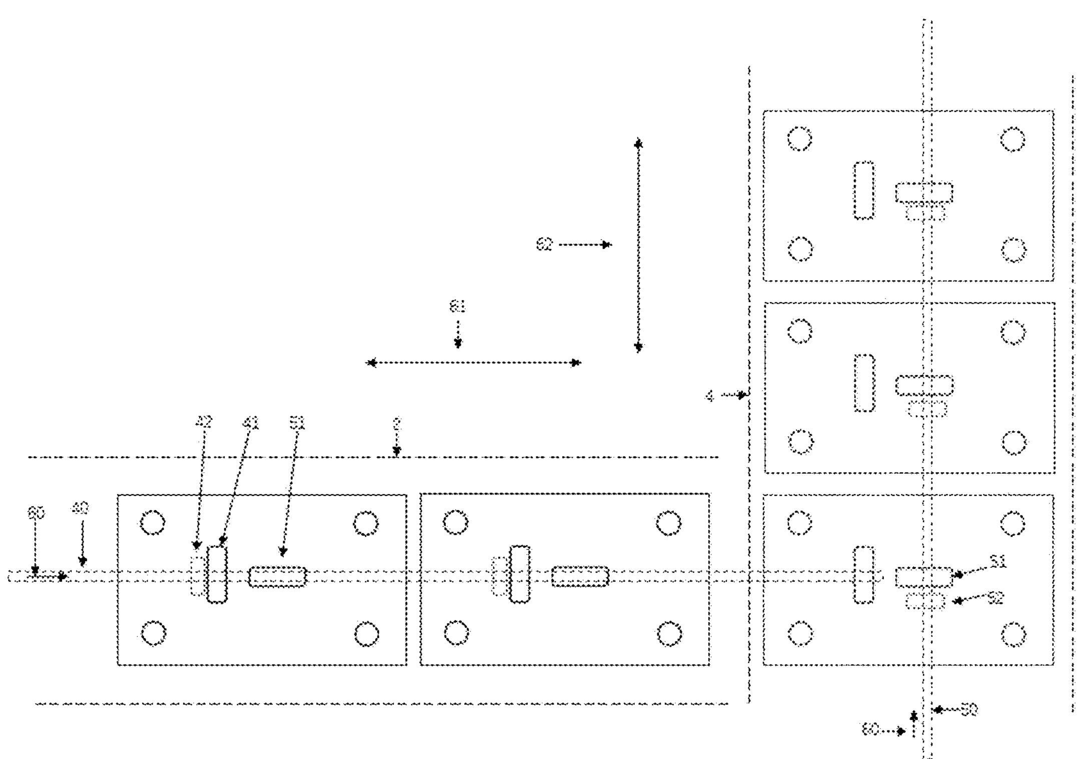
FIG. 7 is a structural schematic diagram of a circular moving layout structure of stacked biological culture trays on a ground according to embodiment 5 of the disclosure.

As shown in FIG. 7, the difference between the circular moving method for stacked biological culture trays on a ground in Embodiment 5 and Embodiment 3 is that, a first connecting mechanism 41 and a second connecting mechanism 51 for chain traction are arrange at intervals at a bottom of the universal wheel tray 20, sinking slits of being low than the ground are arranged in the tray array area 2 along the first direction 61 and in the waiting transfer area 4 along the second direction 62, the sinking slits are used in cooperation with universal wheels 23 of the universal wheel tray 20, the universal wheel tray 20 is capable of spanning the sinking slits, and a first chain sprocket assembly 40 is arranged in a sinking slit of the tray array area 2, the first chain sprocket assembly 40 is provided with a first matching structure 42 matched with the first connecting mechanism 41, and the first connecting mechanism 41 and the first matching structure 42 are capable of being connected or separated according to instructions; a second chain sprocket assembly 50 is arranged in a sinking slit of the waiting transfer area 4, and the second chain sprocket assembly 50 is provided with a second matching structure 52 matched with the second connecting mechanism 51, and the second connecting mechanism 51 and the second matching structure 52 are capable of being connected or separated according to instructions; the circular moving method for stacked biological culture trays on a ground includes:

when preset operation is necessary to performed on the stacked biological culture tray bodies 13 in the preset tray array area 2, the first chain sprocket assembly 40 is firstly started to drive the first matching structure 42 to rotate in a direction of the waiting transfer area 4, the first connecting mechanism 41 of a universal wheel tray 20 closest to the waiting transfer area 4 is firstly connected with the first matching structure 42 in an order from near to far, and the first chain sprocket assembly 40 is continuously rotated in a direction of the waiting transfer area 4, until the second connecting mechanism 51 of the universal wheel tray 20 moves to a position corresponding to the second chain sprocket assembly 50 in the waiting transfer area 4, so that the first matching structure 42 is separated from the first connecting mechanism 41, the second chain sprocket assembly 50 is started to drive the second matching structure 52 to approach the second connecting mechanism 51, so that the second matching structure 52 is connected with the second connecting mechanism 51, and the second chain sprocket assembly 50 is started to drive the universal wheel tray 20 to move to a predetermined position in the temporary tray array area 5, so that the second matching structure 52 and the second connecting mechanism 51 are separated;

and so on, until all the stacked biological culture tray bodies 13 in the tray array area 2 are transferred to the temporary tray array area 5 in the waiting transfer area 4 one by one;

after the preset operation device completes preset operation on the stacked biological culture tray bodies 13 by the tray reversing area 6, the second chain sprocket assembly 50 is firstly started in an order from near to far, so that a second connecting mechanism 51 of a universal wheel tray 20 closest to the empty tray array area 2 is connected with a second matching structure 52, and the second chain sprocket assembly 50 is continuously rotated in a direction of the tray array area 2 until the first connecting mechanism 41 of the universal wheel tray 20 moves a position corresponding to the first chain sprocket assembly 40, so that the second matching structure 52 is separated from the second connecting mechanism 51, then the first chain sprocket assembly 40 is started, so that first matching structure 42 is connected with the first connecting mechanism 41, and the first chain sprocket assembly 40 is started to drive the universal wheel tray 20 to transfer to a predetermined position in the tray array area 2, so as to separate the first matching structure 42 from the first connecting mechanism 41;

and so on, until all the stacked biological culture tray bodies 13 in the waiting transfer area 4 are transferred to the empty tray array area 2 one by one.

Embodiment 6

Figure 8:
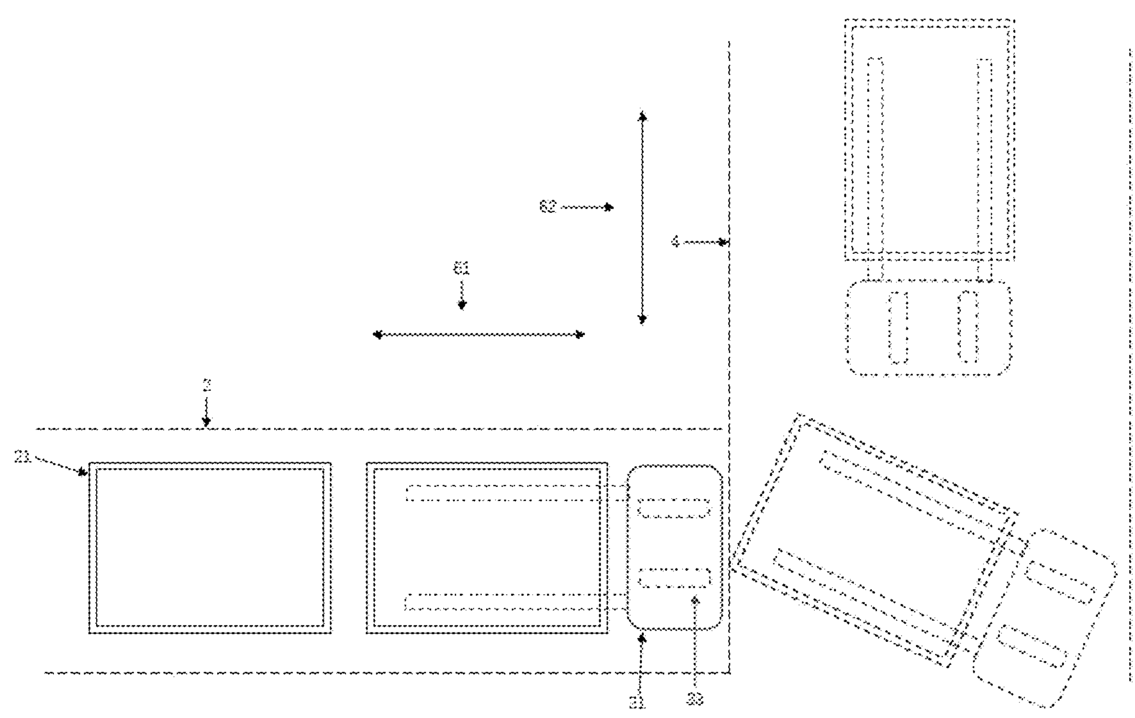
FIG. 8 is a structural schematic diagram of a circular moving layout structure of stacked biological culture trays on a ground according to embodiment 6 of the disclosure.

As shown in FIG. 8, the circular moving method for stacked biological culture trays on a ground in Embodiment 6 adopts the circular moving layout structure of stacked biological culture trays on a ground, carrying devices are further included, the bottom of the carrying device 31 is provided with carrying device drive wheels 33, where the stacked biological culture tray body includes a tray 21 arranged at a bottom, and the circular moving method for stacked biological culture trays on a ground includes:

when preset operation is necessary to performed on the stacked biological culture tray bodies 13 in the preset tray array area 2, the carrying devices 31 are started, it is started from the tray body area 1 closest to the waiting transfer area 4, from near to far, the stacked biological culture tray bodies 13 in the tray array area 2 are lifted one by one by using the carrying devices 31, and then transferred out of the tray array area 2 in the first direction 61, and then transferred to the waiting transfer area 4 in the second direction 62 and placed in the temporary tray array area 5 in sequence until all of the stacked biological culture tray bodies are transferred;

after the preset operation device completes preset operation on the stacked biological culture tray bodies 13 by the tray reversing area 6, the carrying devices are started again, and it is started from one of the tray body area 1 farthest from the waiting transfer area 4, from far to near, the stacked biological culture tray bodies 13 in the waiting transfer area 4 are lifted one by one with the carrying device 31, and then transferred out of the waiting transfer area 4 in the second direction 62, and then transferred to an original tray array area 2 in the first direction 61 until all of the stacked biological culture tray bodies are transferred.

Embodiment 7

Figure 9:
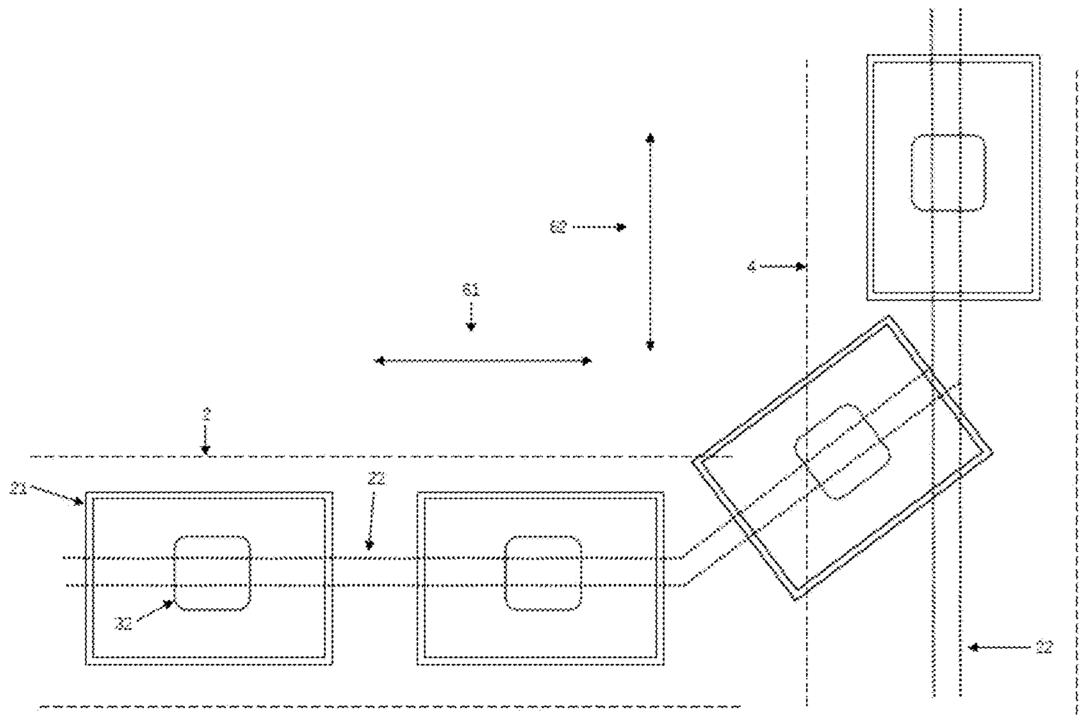
FIG. 9 is a structural schematic diagram of a circular moving layout structure of stacked biological culture trays on a ground according to embodiment 7 of the disclosure.

As shown in FIG. 9, the circular moving method for stacked biological culture trays on a ground in Embodiment 7 adopts the circular moving layout structure of stacked biological culture trays on a ground, wheel-rail carrying devices are includes, where the stacked biological culture tray body includes a tray arranged at a bottom, and sinking narrow rails 22 lower than the ground are arranged in the tray array area 2 along the first direction 61 and in the waiting transfer area 4 along the second direction 62, a sinking narrow rail 22 in the first direction 61 and a sinking narrow rail 22 in the second direction 62 are communicated with each other, and the wheel-rail carrying devices 32 are capable of moving along the first direction 61 or the second direction 62 on the sinking narrow rails 22, the circular moving method for stacked biological culture trays on a ground includes:

when preset operation is necessary to perform on the stacked biological culture tray bodies 13 in the preset tray array area 2, the wheel-rail carrying device 32 is started, and it is started from the tray body area 1 closest to the waiting transfer area 4, from near to far, the stacked biological culture tray bodies 13 in the tray array area 2 sequentially are lifted by the wheel-rail carrying device 32 along the sinking narrow rails 22, and transferred to the temporary tray area 5 in the waiting transfer area 4, until all of the stacked biological culture tray bodies are transferred;

after the preset operation device completes preset operation on the stacked biological culture tray bodies 13 by the tray reversing area 6, the wheel-rail carrying devices 32 are started again, and it is started from one of the tray body area 1 farthest from the waiting transfer area 4, from far to near, the stacked biological culture tray bodies 13 in the waiting transfer area 4 sequentially are lifted by the wheel-rail carrying device 32 along the sinking narrow rails 22, and transferred to an original tray array area 2, until all of stacked biological culture tray bodies are transferred.

Embodiment 8

Figure 10:
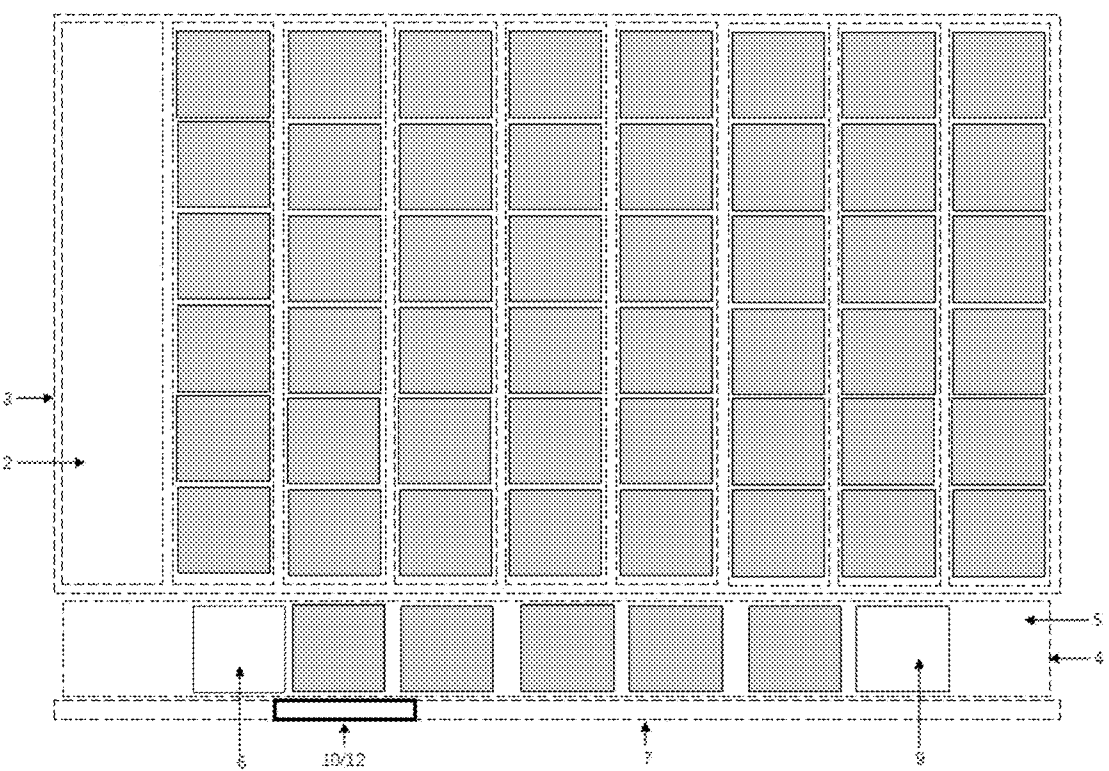
FIG. 10 is a structural schematic diagram of a circular moving layout structure of stacked biological culture trays on a ground according to embodiment 8 of the disclosure.
Figure 11:
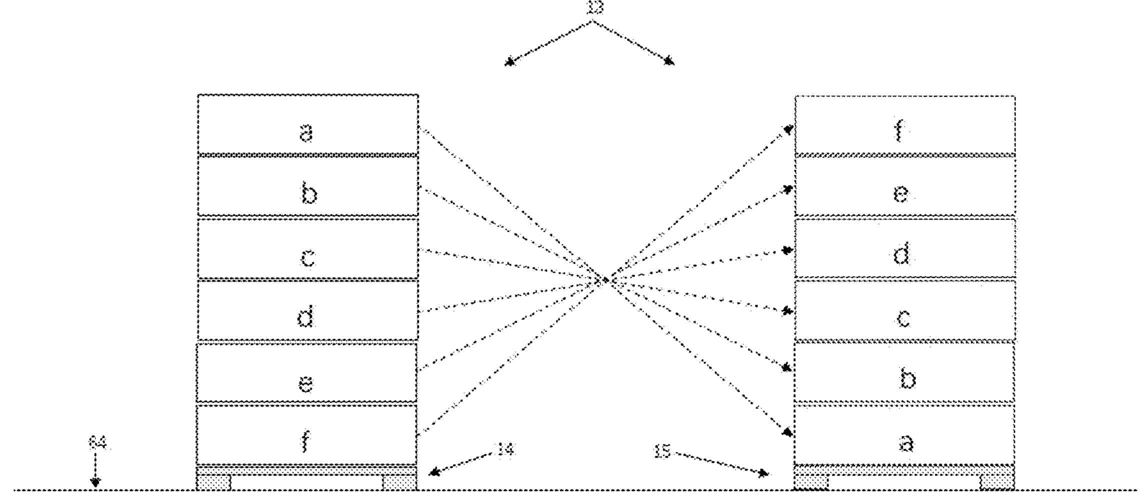
FIG. 11 is a structural schematic diagram of a circular moving layout structure of stacked biological culture trays on a ground according to embodiment 8 of the disclosure.

As shown in FIG. 10 and FIG. 11, a circular moving method for stacked biological culture trays on a ground in Embodiment 8 adopts the circular moving layout structure of stacked biological culture trays on a ground, a reversal tray 15 is included, the stacked biological culture tray body 13 includes a body tray 14 and multiple biological culture trays overlapped on the body tray 14, and a biological culture tray located at a bottommost is detachably connected with the body tray 14, the reversal tray 15 and the body tray 14 are capable of being used interchangeably, as shown in FIG. 11, the reversal tray 15 and the body tray 14 are exchanged when they are both placed on the ground 64, and the tray reversing area 6 is arranged at at least one end of the temporary tray array area 5 in the waiting transfer area 4, the circular moving method for stacked biological culture tray bodies 13 by the reciprocating operation device 10 includes:

the reversal tray 15 is placed in the tray reversing area 6;

all the stacked biological culture tray bodies 13 in the preset tray array area 2 are transferred to the temporary tray array area 5;

the reciprocating operation device 10 is moved to a temporary tray array area 5 adjacent to the tray reversing area 6 and corresponded to one of the stacked biological culture tray bodies 13;

a performing mechanism of the reciprocating operation device 10 is started, preset operation on each of the biological culture trays in one of the stacked biological culture tray bodies 13 is sequentially performed from top to bottom, and each of biological culture trays of completing preset operation is sequentially placed on the reversal tray 15 in the tray reversing area 6 from bottom to top, so that a body tray 14 of stacked biological culture tray body 13 of completing preset operation becomes a new reversal tray 15, a corresponding area becomes a new tray reversing area 6, and an original tray reversing area 6 becomes a part of the temporary tray array area 5;

then the reciprocating operation device 10 is moved to a temporary tray array area 5 adjacent to the new tray reversing area 9, and corresponded to a stacked biological culture tray body 13 waiting for preset operation;

a performing mechanism of the reciprocating operation device is started, preset operation is sequentially performed on each of biological culture trays in one of the stacked biological culture tray bodies 13 waiting for preset operation from top to bottom, and each of biological culture trays of completing the preset operation is sequentially placed on a new reversal tray 15 on a new tray reversing area 9 from bottom to top, so that the body tray 14 of the stacked biological culture tray body 13 of completing preset operation becomes into another new reversal tray 15, a corresponding area becomes another new tray reversing area 6, and an original new tray reversing area 9 becomes a part of the temporary tray array area 5;

and so on, until all stacked biological culture tray bodies 13 waiting for preset operation in the temporary tray array area 5 complete preset operation, a body tray 14 of a stacked biological culture tray body 13 of completing the preset operation finally becomes a last new reversal tray 15, and a corresponding area becomes a last new tray reversing area 6; and each of the stacked biological culture tray bodies 13 of completing preset operation in the temporary tray array area 5 is sequentially transferred to the original tray array area 2.

Embodiment 9

Figure 12:
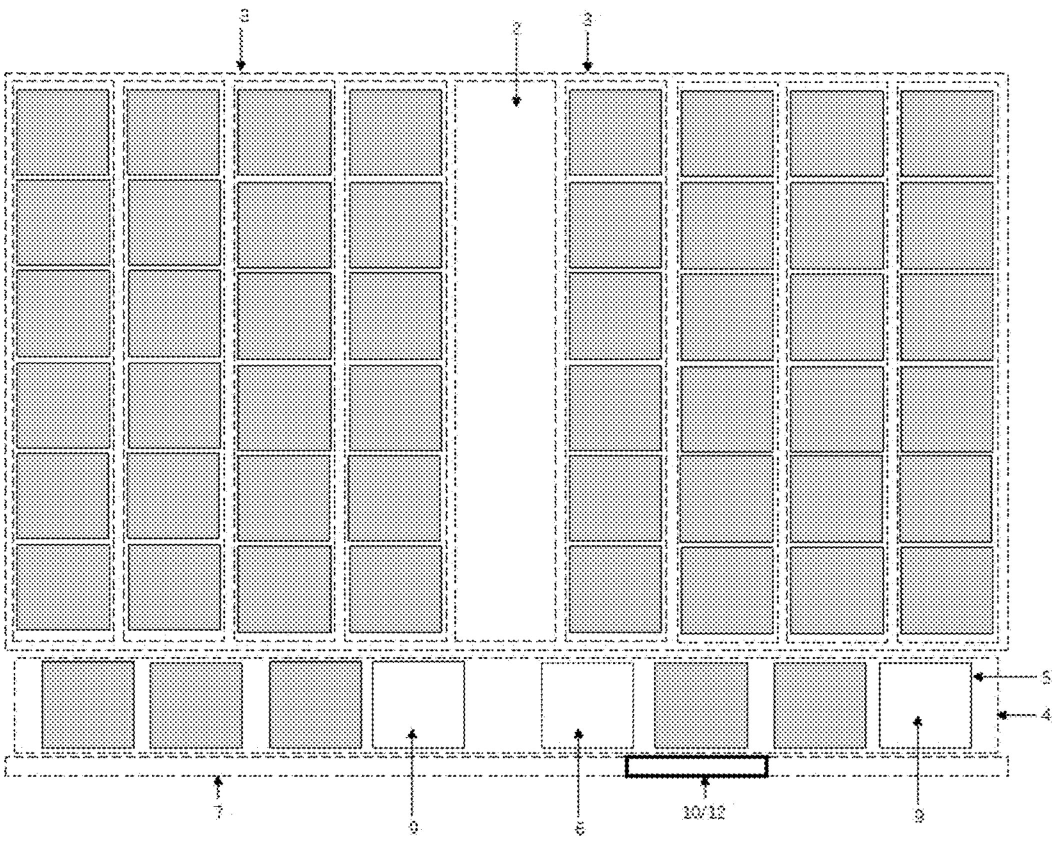
FIG. 12 is a structural schematic diagram of a circular moving layout structure of stacked biological culture trays on a ground according to embodiment 9 of the disclosure.

As shown in FIG. 12, a circular moving method for stacked biological culture trays on a ground in Embodiment 9 adopts the circular moving layout structure of stacked biological culture trays on a ground, a reversal tray 15 is included, where each of the stacked biological culture tray bodies 13 includes a body tray 14 and multiple biological culture trays overlapped on the body tray 14, and a biological culture tray located at a bottommost is detachably connected with the body tray 14, the reversal tray 15 and the body tray 14 are capable of being used interchangeably, and the tray reversing area 6 is arranged in a middle of the temporary tray array area 5 in the waiting transfer area 4, and is located near the tray array area 2 of being preset to wait for preset operation, the circular moving method for stacked biological culture tray bodies by the reciprocating operation device 10 includes:

a part of stacked biological culture tray bodies 13 in the preset tray array area 2 are firstly transferred to the temporary tray array area 5 on one side of the tray array area 2 in the waiting transfer area 4, then another part of stacked biological culture tray bodies 13 in the preset tray array area 2 are transferred to the temporary tray array area 5 on an other side of the preset tray array area 2 in the waiting transfer area 4, and the tray reversing area 6 is set at a position near an intersection of the preset tray array area 2 and the waiting transfer area 4;

the reversal tray 15 is placed in the tray reversing area 6;

the reciprocating operation device 10 is moved to a temporary tray array area 5 adjacent to the tray reversing area 6 at one side of the tray reversing area 6 and corresponded to one of the stacked biological culture tray bodies;

a performing mechanism of the reciprocating operation device 10 is started, preset operation is sequentially performed on each of biological culture trays in one of the stacked biological culture tray bodies 13 waiting for preset operation from top to bottom, and each of biological culture trays of completing preset operation is sequentially placed on a reversal tray 15 on a tray reversing area 6 from bottom to top, so that the body tray 14 of the stacked biological culture tray body 13 of completing preset operation becomes into another new reversal tray 15, a corresponding area becomes another new tray reversing area 6, and an original tray reversing area 6 becomes a part of the temporary tray array area 5;

then the reciprocating operation device 10 is moved to a temporary tray array area 5 adjacent to the new tray reversing area 9, and corresponded to the stacked biological culture tray body 13 waiting for preset operation;

a performing mechanism of the reciprocating operation device 10 is started, preset operation is sequentially performed on each of the biological culture trays in one of the stacked biological culture disc bodies 13 waiting for preset operation from top to bottom, and each of the biological culture trays of completing preset operation is sequentially placed on a new reversal tray 15 on a new tray reversing area 9 from bottom to top, so that the body tray of the stacked biological culture disc body 13 of completing preset operation becomes another new reversal tray 15, a corresponding area becomes another new tray reversing area 6, and an original new tray reversing area 9 becomes a part of the temporary tray array area 5;

and so on, until all the stacked biological culture tray bodies 13 waiting for preset operation in the temporary tray array area 5 at one side of the tray reversing area 6 completes preset operation, the body tray 14 of one of the stacked biological culture tray bodies 13 of completing the preset operation finally becomes another new reversal tray 15, and corresponding area becomes another new tray reversing area 6;

each of the stacked biological culture tray bodies 13 of having completed preset operation in the temporary tray array area 5 is sequentially transferred to an original tray array area 2;

another new reversal tray 15 is transferred to an opposite end of a temporary tray array area 5 on an other side;

similarly, the reciprocating operation device 10 is moved to the temporary tray array area 5 on the other side and corresponding to the stacked biological culture tray body 13 adjacent to another new reversal tray 15;

above operation flow is repeated, until remaining stacked biological culture tray bodies 13 complete preset operation and sequentially transferred to an original tray array area.

Embodiment 10

Figure 13:
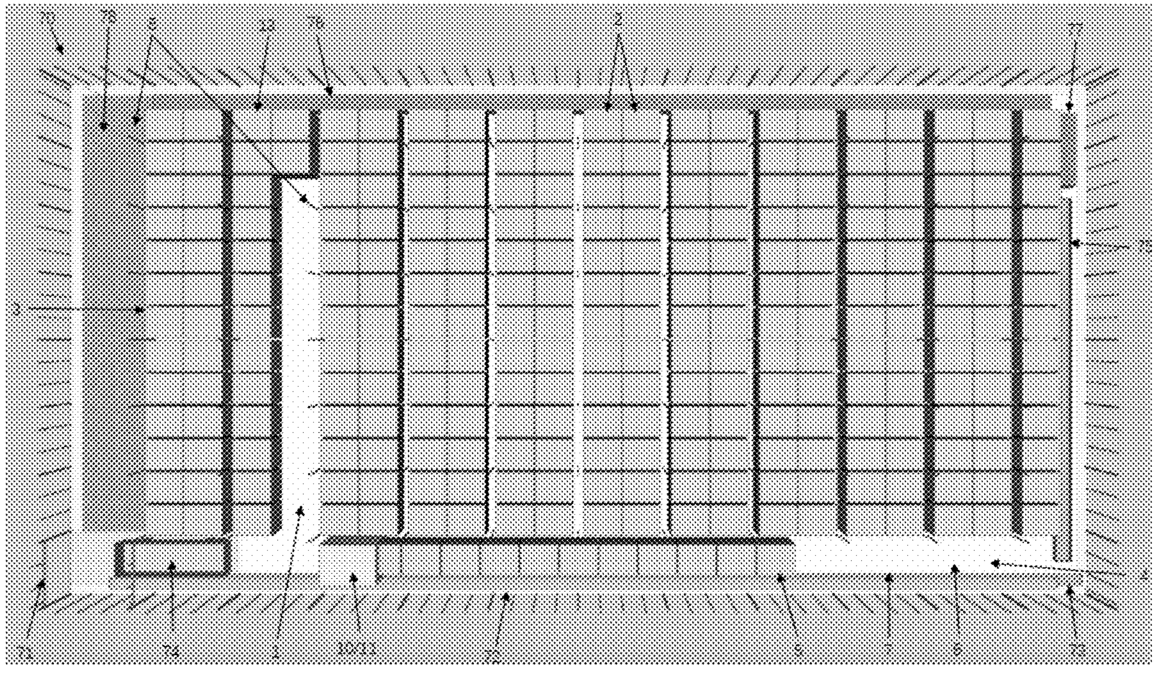
FIG. 13 is a structural schematic diagram of a circular moving layout structure of stacked biological culture trays on a ground according to embodiment 10 of the disclosure.

As shown in FIG. 13, the pasture plant 70 of this Embodiment 10 is a plant stereoscopic culture plant for producing barley/wheat sprouts about 7 days old, and adopts the circulating operation method of the stacked biological culture trays on a ground, and operates on the circulating moving layout structure of the stacked biological culture trays on a ground, and further includes a biological harvesting and transferring parking space 74, a biological harvesting and transferring conveyor belt 72, a biological species sowing and supplying conveyor belt 73, a biological species processing facility 75 and a biological cultivation water supplying facility 76, where the biological harvesting and transferring parking space 74 is arranged at preset ends of the waiting transfer area 4 and the operation area 7 in the second direction 62, arranged near the across door of the plant for exporting pasture products and importing pasture seeds, and the biological harvesting and transferring conveyor belt 72 is arranged corresponding to the operation area 7 and arranged outside the operation area 7, and is used for receiving pasture products harvested from the stacked biological culture tray bodies 13 by the reciprocating operation device 10 and transferring to the biological harvesting and transferring parking space 74, so as to be quickly loaded and transported away. The biological species processing facility 75 is arranged outside one side of the display area 3 away from the biological harvesting and transferring parking space 74, and the biological species sowing and feeding conveyor belt 73 is arranged corresponding to the operation area 7 and arranged outside the operation area 7, the biological species sowing and supplying conveyor belt 73 is arranged in parallel with the biological species harvesting and transferring conveyor belt 72 and is located at one side or below the biological species harvesting and transferring conveyor belt 72; one end of the biological species sowing and supplying conveyor belt 73 reaches the biological species harvesting and transferring parking space 74, and an other end reaches the biological species processing facility 75 for receiving pasture seeds from biological harvesting and transferring parking space 74, and transferring the seeds to the biological species processing facility 75; and the biological cultivation water supplying facility 76 is arranged outside one side of the display area 3 away from the waiting transfer area 4, and is used for supplying the stacked biological culture trays in each of the tray array area 2 with water required for cultivating pasture.

Where, the pasture plant 70 of this Embodiment 10 further includes a biological cultivation nutrient supply facility 77 and a control area 78, the control area 78 is arranged outside the side of the display area 3 close to the biological harvesting and transferring parking space 74, and the biological cultivation nutrient supply facility 77 is also arranged outside the side of the display area 3 away from the biological harvesting and transferring parking space 74, and is adjacent to the biological seed processing facility 75, and access doors of plant 71 are arranged at the position opposite to the biological harvesting and transferring parking space 74.

The circular moving layout structure, method for the stacked biological culture tray, and a pasture plant of the disclosure are provided with the display area, the waiting transfer area and the operation area, and the waiting transfer area includes the temporary tray array area and at least one tray reversing area, and through the cooperation of the temporary tray array area and the tray reversing area, the utilization rate of the biological stereoscopic culture space are greatly improved, various preset operations including biological species sowing and/or biological harvesting operations may be conveniently performed on each stacked biological culture tray body, the overall structural design is reasonable, the biological culture space can be fully utilize, the cost is effectively saved, the use is convenient, and the biological stereoscopic culture plant is suitable for popularization and application.

The above-mentioned embodiments only describe the preferred mode of the disclosure, and do not limit the scope of the disclosure. Under the premise of not departing from the design spirit of the disclosure, various modifications and improvements made by ordinary skilled in the field to the technical scheme of the disclosure shall fall within the protection scope determined by the claims of the disclosure.

What is claimed is:

1. A circular moving layout structure of stacked biological culture trays on a ground, comprising display areas, a waiting transfer area and an operation area, wherein each of the display areas comprises a plurality of tray array areas, each of the tray array areas comprises a plurality of tray body areas, and the plurality of tray body areas are arranged in a single row along a first direction, and one of stacked biological culture tray bodies is correspondingly placed in each of the tray body areas in each of the tray array areas, and the stacked biological culture tray bodies are used for cultivating preset organisms, vertical projection areas of each of stacked biological culture tray bodies in each of the tray array areas on a ground are connected in a rectangular outline, each of the tray array areas is rectangular with long sides in the first direction, and a plurality of the tray array areas are arranged as the display areas along a second direction, and the first direction and the second direction are vertically arranged;

the waiting transfer area comprises a temporary tray array area and at least one tray reversing area, wherein the temporary tray array area is used for temporarily accommodating all the stacked biological culture tray bodies in at least one of the tray array areas, and the tray reversing area is used for temporarily accommodating at least one of the stacked biological culture tray bodies; the tray reversing area is arranged at an end of the temporary tray array area and communicates with the temporary tray array area from one side, or, the tray reversing area is arranged in a middle of the temporary tray reversing area to divide the temporary tray array area into two sections and communicate with the temporary tray array area from two sides; the temporary tray array area is used in cooperation with the tray reversing area, so as to perform preset operation on each of the stacked biological culture tray bodies; vertical projection areas of all the stacked biological culture tray bodies accommodated in the waiting transfer area on the ground are connected in a rectangular outline, the waiting transfer area is rectangular with long sides in the second direction, and a length of the waiting transfer area is greater than a sum of a length of at least one of the tray array areas and a length of the tray reversing area; a long side of the waiting transfer area corresponds to a short side of each of the tray array areas in each of the display areas, a width of the waiting transfer area is greater than or equal to a maximum side length of each of the tray body areas, the waiting transfer area is interconnected with each of the tray array areas in each of the display areas, and all the stacked biological culture tray bodies in each of the tray array areas perform barrier-free sequential circular movement between the tray array areas and the waiting transfer area in a full-in and full-out manner;

the waiting transfer area is connected with the operation area for use;

the operation area is used for arranging a reciprocating operation device of being capable of moving back and forth, and the reciprocating operation device moves back and forth on two long sides of the waiting transfer area in the second direction; vertical projection areas of the reciprocating operation device on the ground are connected in a rectangular outline during reciprocating movement; the operation area covers the waiting transfer area; a width of the operation area is greater than a width of the waiting transfer area; a length of the operation area is greater than or equal to a length of the waiting transfer area, so that the reciprocating operation device is capable of riding across the waiting transfer area for reciprocating movement, and during reciprocating movement, preset operation is performed on the stacked biological culture tray bodies in any position of the temporary tray array area by the tray reversing area, and a barrier-free movement of the stacked biological culture tray bodies between each of the tray array areas and the waiting transfer area is not hindered; or, the operation area is used for arranging reciprocating operation device of being capable of moving reciprocally, and the reciprocating operation device moves reciprocally along a long side of the waiting transfer area in the second direction, and vertical projection areas of the reciprocating operation device on the ground during reciprocating movement are connected in a rectangular outline, and the operation area is adjacent to the waiting transfer area, and a length of the operation area is greater than or equal to a length of the waiting transfer area, so that the reciprocating operation device is capable of moving reciprocally along a side of the waiting transfer area, and during reciprocating movement, preset operation is performed on the stacked biological culture tray bodies in any position of the temporary tray array area by the tray reversing area, and a barrier-free movement of the stacked biological culture tray bodies between the tray array areas and the waiting transfer area is not hindered;

one of the display areas is configured in one waiting transfer area and one operation area, and one of the display areas is arranged on one side of one long side of the waiting transfer area and the operation area; or, two the display areas are configured in one waiting transfer area and one operation area, and one of the display areas is respectively arranged on each side of two long sides of the waiting transfer area and the operation area.

2. The circular moving layout structure of stacked biological culture trays on a ground according to claim 1, further comprising column structures, wherein each of the display areas comprises a plurality of rows of the column structures, one or two of the tray array areas are arranged between two adjacent rows of the column structures in the first direction, and at least one side of each of the tray body areas in each of the tray array areas corresponds to one of the column structures, so that the stacked biological culture tray bodies on the tray body areas are connected with the column structures according to a preset scheme, and the waiting transfer area and the operation area are arranged between two adjacent rows of the column structures in the second direction;

or, more than three tray array areas are arranged between two adjacent rows of the column structures in the first direction, and the waiting transfer area and the operation area are arranged between two adjacent rows of the column structures in the second direction.

3. The circular moving method for stacked biological culture trays on a ground, adopting the circular moving layout structure of stacked biological culture trays on a ground according to claim 2, wherein each of the stacked biological culture tray bodies comprises a universal wheel tray arranged at a bottom, ground suitable for the universal wheel tray to walk in a barrier-free way is arranged in each of the tray array areas along the first direction and the waiting transfer area along the second direction, the universal wheel tray is used in cooperation with the ground, and a circular moving method for the stacked biological culture trays on the ground comprises:

applying force to the universal wheel tray of each of the stacked biological culture tray bodies in a preset manner when the stacked biological culture tray bodies in a preset tray array area are performed preset operation, so that the universal wheel tray moves in a direction of applying force, and starting from a tray body area nearest from the waiting transfer area, transferring the stacked biological culture tray bodies in the tray array areas to the temporary tray array area in the waiting transfer area one by one from near to far, until all the stacked biological culture tray bodies are transferred;

applying force to the universal wheel tray of each of the stacked biological culture tray bodies again after preset operation device completes preset operation on the stacked biological culture tray bodies by the tray reversing area, so that the universal wheel tray moves in the direction of applying force, and starting from a tray body area farthest from the waiting transfer area, transferring the stacked biological culture tray bodies in the waiting transfer area to an original tray array area one by one from far to near, until all the stacked biological culture tray bodies are transferred;

or further comprising carrying devices, wherein each of the stacked biological culture tray bodies comprises a tray arranged at a bottom, and the circular moving method for stacked biological culture trays on a ground comprises:

starting the carrying devices when preset operation is necessary to performed on the stacked biological culture tray bodies in the preset tray array area, starting from one of the tray body areas closest to the waiting transfer area, from near to far, lifting the stacked biological culture tray bodies in the tray array area one by one by using the carrying devices, and then transferring out of the tray array area in the first direction, and then transferring to the waiting transfer area in the second direction and placing in the temporary tray array area in sequence until all of the stacked biological culture tray bodies are transferred;

starting the carrying devices again after the preset operation device completes preset operation on the stacked biological culture tray bodies by the tray reversing area, and starting from one of the tray body areas farthest from the waiting transfer area, from far to near, lifting the stacked biological culture tray bodies in the waiting transfer area one by one with the carrying devices, and then transferring out of the waiting transfer area in the second direction, and then transferring to an original tray array area in the first direction until all of the stacked biological culture tray bodies are transferred;

or further comprising wheel-rail carrying devices, wherein each of the stacked biological culture tray bodies comprises a tray arranged at a bottom, and sinking narrow rails lower than the ground are arranged in the tray array areas along the first direction and in the waiting transfer area along the second direction, a sinking narrow rail in the first direction and a sinking narrow rail in the second direction are communicated with each other, and the wheel-rail carrying devices are capable of moving along the first direction or the second direction on the sinking narrow rails, the circular moving method for stacked biological culture trays on a ground comprises:

starting the wheel-rail carrying devices when preset operation is necessary to perform on the stacked biological culture tray bodies in the preset tray array area, and starting from one of the tray body areas closest to the waiting transfer area, from near to far, lifting the stacked biological culture tray bodies in the tray array areas sequentially by the wheel-rail carrying devices along the sinking narrow rails, and transferring to the temporary tray area in the waiting transfer area until all of the stacked biological culture tray bodies are transferred;

starting the wheel-rail carrying devices again after the preset operation device completes preset operation on the stacked biological culture tray bodies by the tray reversing area, and starting from one of the tray body areas farthest from the waiting transfer area, from far to near, lifting the stacked biological culture tray bodies in the waiting transfer area sequentially by the wheel-rail carrying devices along the sinking narrow rails, and transferring to an original tray array area until all of stacked biological culture tray bodies are transferred;

or further comprising a reversal tray, wherein each of the stacked biological culture tray bodies comprises a body tray and a plurality of biological culture trays overlapped on the body tray, and a biological culture tray located at a bottommost is detachably connected with the body tray, the reversal tray and the body tray are capable of being used interchangeably, and the tray reversing area is arranged at at least one end of the temporary tray array area in the waiting transfer area, the circular moving method for stacked biological culture tray bodies on a ground by the reciprocating operation device comprises:

placing the reversal tray in the tray reversing area;

transferring all the stacked biological culture tray bodies in the preset tray array area to the temporary tray array area;

moving the reciprocating operation device to a temporary tray array area adjacent to the tray reversing area and corresponding to one of the stacked biological culture tray bodies;

starting a performing mechanism of the reciprocating operation device, sequentially performing preset operation on each of the biological culture trays in one of the stacked biological culture tray bodies from top to bottom, and sequentially placing each of biological culture trays of completing preset operation on the reversal tray in the tray reversing area from bottom to top, so that a body tray of stacked biological culture tray body of completing preset operation becomes a new reversal tray, a corresponding area becomes a new tray reversing area, and an original tray reversing area becomes a part of the temporary tray array area;

then moving the reciprocating operation device to a temporary tray array area adjacent to the new tray reversing area, and corresponding to a stacked biological culture tray body waiting for preset operation;

starting a performing mechanism of the reciprocating operation device, sequentially performing preset operation on each of biological culture trays in one of the stacked biological culture tray bodies waiting for preset operation from top to bottom, and sequentially placing each of biological culture trays of completing the preset operation on a new reversal tray on a new tray reversing area from bottom to top, so that the body tray of each of the stacked biological culture tray bodies of completing preset operation becomes into another new reversal tray, a corresponding area becomes another new tray reversing area, and an original new tray reversing area becomes a part of the temporary tray array area;

and so on, until all stacked biological culture tray bodies waiting for preset operation in the temporary tray array area complete preset operation, a body tray of a stacked biological culture tray body of completing the preset operation finally becomes a last new reversal tray, and a corresponding area becomes a last new tray reversing area; and sequentially transferring each of the stacked biological culture tray bodies of completing preset operation in the temporary tray array area to the original tray array area;

or further comprising a reversal tray, wherein each of the stacked biological culture tray bodies comprises a body tray and a plurality of biological culture trays overlapped on the body tray, and a biological culture tray located at a bottommost is detachably connected with the body tray, the reversal tray and the body tray are capable of being used interchangeably, and the tray reversing area is arranged in a middle of the temporary tray array area in the waiting transfer area, and is located near the tray array area of being preset to wait for preset operation, the circular moving method for stacked biological culture tray bodies on a ground by the reciprocating operation device comprises:

firstly transferring a part of stacked biological culture tray bodies in the preset tray array area to the temporary tray array area on one side of the tray array area in the waiting transfer area, then transferring another part of stacked biological culture tray bodies in the preset tray array area to the temporary tray array area on an other side of the tray array area in the waiting transfer area, and setting the tray reversing area at a position near an intersection of the tray array area and the waiting transfer area;

placing the reversal tray in the tray reversing area;

moving the reciprocating operation device to a temporary tray array area adjacent to the tray reversing area at one side of the tray reversing area and corresponding to one of the stacked biological culture tray bodies;

starting a performing mechanism of the reciprocating operation device, sequentially performing preset operation on each of biological culture trays in one of the stacked biological culture tray bodies waiting for preset operation from top to bottom, and sequentially placing each of biological culture trays of completing preset operation on a reversal tray on a tray reversing area from bottom to top, so that the body tray of each of the stacked biological culture tray bodies of completing preset operation becomes into another new reversal tray, a corresponding area becomes another new tray reversing area, and an original tray reversing area becomes a part of the temporary tray array area;

then moving the reciprocating operation device to a temporary tray array area adjacent to the new tray reversing area, and corresponding to one of the stacked biological culture tray bodies waiting for preset operation;

starting a performing mechanism of the reciprocating operation device, sequentially performing preset operation on each of the biological culture trays in one of the stacked biological culture disc bodies waiting for preset operation from top to bottom, and sequentially placing each of the biological culture trays of completing preset operation on a new reversal tray on a new tray reversing area from bottom to top, so that the body tray of each of the stacked biological culture disc bodies of completing preset operation becomes another new reversal tray, a corresponding area becomes another new tray reversing area, and an original new tray reversing area becomes a part of the temporary tray array area;

and so on, until all the stacked biological culture tray bodies waiting for preset operation in the temporary tray array area at one side of the tray reversing area completes preset operation, the body tray of one of the stacked biological culture tray bodies of completing the preset operation finally becomes another new reversal tray, and corresponding area becomes another new tray reversing area;

sequentially transferring each of the stacked biological culture tray bodies of having completed preset operation in the temporary tray array area to an original tray array area;

transferring another new reversal tray to an opposite end of a temporary tray array area on an other side;

similarly, moving the reciprocating operation device to the temporary tray array area on the other side and corresponding to one of the stacked biological culture tray bodies adjacent to another new reversal tray;

repeating above operation flow until remaining stacked biological culture tray bodies complete preset operation and sequentially transferring to an original tray array area.

4. The circular moving method for stacked biological culture trays on a ground according to claim 3, wherein the tray array area and the waiting transfer area are provided with navigation signals of being mutually connected and used in cooperation, and the navigation signals are used in cooperation with carrying robots, and the universal wheel tray is applied force by each of the carrying robots, and the circular moving method for stacked biological culture trays on a ground comprises:

starting the carrying robots when preset operation is necessary to performed on the stacked biological culture tray bodies in the preset tray array area, and starting from a tray body area nearest from the waiting transfer area, lifting or semi-lifting the stacked biological culture tray bodies in the tray array areas one by one from near to far by using the carrying robots according to the navigation signals, and transferring out of the tray array areas in the first direction, and then transferring to the waiting transfer area in the second direction and sequentially placing in the temporary tray array area until all of the stacked biological culture tray bodies are transferred;

staring the carrying robots again after the preset operation device completes the preset operation on the stacked biological culture tray bodies by the tray reversing area, and starting from a tray body area farthest from the waiting transfer area, lifting or semi-lifting the stacked biological culture tray bodies in the waiting transfer area one by one from far to near by using the carrying robots according to the navigation signals, and transferring out of the tray array areas in the second direction, and then transferring to the waiting transfer area in the second direction and transferring to an original tray array area along the first direction until all of the stacked biological culture tray bodies are transferred.

5. The circular moving method for stacked biological culture trays on a ground according to claim 3, wherein a first connecting mechanism and a second connecting mechanism for chain traction are arrange at intervals at a bottom of the universal wheel tray, sinking slits of being low than the ground are arranged in the tray array areas along the first direction and in the waiting transfer area along the second direction, the sinking slits are used in cooperation with universal wheels of the universal wheel tray, the universal wheel tray is capable of spanning the sinking slits, and a first chain sprocket assembly is arranged in a sinking slit of the tray array areas, the first chain sprocket assembly is provided with a first matching structure matched with the first connecting mechanism, and the first connecting mechanism and the first matching structure are capable of being connected or separated according to instructions; a second chain sprocket assembly is arranged in a sinking slit of the waiting transfer area, and the second chain sprocket assembly is provided with a second matching structure matched with the second connecting mechanism, and the second connecting mechanism and the second matching structure are capable of being connected or separated according to instructions; the circular moving method for stacked biological culture trays on a ground comprises:

firstly starting the first chain sprocket assembly to drive the first matching structure to rotate in a direction of the waiting transfer area when preset operation is necessary to performed on the stacked biological culture tray bodies in the preset tray array area, firstly connecting the first connecting mechanism of a universal wheel tray closest to the waiting transfer area with the first matching structure in an order from near to far, and continuously rotating the first chain sprocket assembly in a direction of the waiting transfer area, until the second connecting mechanism of the universal wheel tray moves to a position corresponding to the second chain sprocket assembly in the waiting transfer area, so that the first matching structure is separated from the first connecting mechanism, starting the second chain sprocket assembly to drive the second matching structure to approach the second connecting mechanism, so that the second matching structure is connected with the second connecting mechanism, and starting the second chain sprocket assembly to drive the universal wheel tray to move to a predetermined position in the temporary tray array area, so that the second matching structure and the second connecting mechanism are separated;

and so on, until all the stacked biological culture tray bodies in the tray array areas are transferred to the temporary tray array area in the waiting transfer area one by one;

after the preset operation device completes preset operation on the stacked biological culture tray bodies by the tray reversing area, firstly starting the second chain sprocket assembly in an order from near to far, so that a second connecting mechanism of a universal wheel tray closest to the tray array area is connected with a second matching structure, and continuously rotating the second chain sprocket assembly in a direction of the tray array area until the first connecting mechanism of the universal wheel tray moves a position corresponding to the first chain sprocket assembly, so that the second matching structure is separated from the second connecting mechanism, then starting the first chain sprocket assembly, so that first matching structure is connected with the first connecting mechanism, and starting the first chain sprocket assembly to drive the universal wheel tray to transfer to a predetermined position in each of the tray array areas, so as to separate the first matching structure from the first connecting mechanism;

and so on, until all the stacked biological culture tray bodies in the waiting transfer area are transferred to the tray array areas one by one.

6. A circular moving method for stacked biological culture trays on a ground, adopting the circular moving layout structure of stacked biological culture trays on a ground according to claim 1, wherein each of the stacked biological culture tray bodies comprises a universal wheel tray arranged at a bottom, ground suitable for the universal wheel tray to walk in a barrier-free way is arranged in each of the tray array areas along the first direction and the waiting transfer area along the second direction, the universal wheel tray is used in cooperation with the ground, and a circular moving method for the stacked biological culture trays on the ground comprises:

applying force to the universal wheel tray of each of the stacked biological culture tray bodies in a preset manner when the stacked biological culture tray bodies in a preset tray array area are performed preset operation, so that the universal wheel tray moves in a direction of applying force, and starting from a tray body area nearest from the waiting transfer area, transferring the stacked biological culture tray bodies in the tray array areas to the temporary tray array area in the waiting transfer area one by one from near to far, until all the stacked biological culture tray bodies are transferred;

applying force to the universal wheel tray of each of the stacked biological culture tray bodies again after preset operation device completes preset operation on the stacked biological culture tray bodies by the tray reversing area, so that the universal wheel tray moves in the direction of applying force, and starting from a tray body area farthest from the waiting transfer area, transferring the stacked biological culture tray bodies in the waiting transfer area to an original tray array area one by one from far to near, until all the stacked biological culture tray bodies are transferred;

or further comprising carrying devices, wherein each of the stacked biological culture tray bodies comprises a tray arranged at a bottom, and the circular moving method for stacked biological culture trays on a ground comprises:

starting the carrying devices when preset operation is necessary to performed on the stacked biological culture tray bodies in the preset tray array area, starting from one of the tray body areas closest to the waiting transfer area, from near to far, lifting the stacked biological culture tray bodies in the tray array area one by one by using the carrying devices, and then transferring out of the tray array area in the first direction, and then transferring to the waiting transfer area in the second direction and placing in the temporary tray array area in sequence until all of the stacked biological culture tray bodies are transferred;

starting the carrying devices again after the preset operation device completes preset operation on the stacked biological culture tray bodies by the tray reversing area, and starting from one of the tray body areas farthest from the waiting transfer area, from far to near, lifting the stacked biological culture tray bodies in the waiting transfer area one by one with the carrying devices, and then transferring out of the waiting transfer area in the second direction, and then transferring to an original tray array area in the first direction until all of the stacked biological culture tray bodies are transferred;

or further comprising wheel-rail carrying devices, wherein each of the stacked biological culture tray bodies comprises a tray arranged at a bottom, and sinking narrow rails lower than the ground are arranged in the tray array areas along the first direction and in the waiting transfer area along the second direction, a sinking narrow rail in the first direction and a sinking narrow rail in the second direction are communicated with each other, and the wheel-rail carrying devices are capable of moving along the first direction or the second direction on the sinking narrow rails, the circular moving method for stacked biological culture trays on a ground comprises:

starting the wheel-rail carrying devices when preset operation is necessary to perform on the stacked biological culture tray bodies in the preset tray array area, and starting from one of the tray body areas closest to the waiting transfer area, from near to far, lifting the stacked biological culture tray bodies in the tray array areas sequentially by the wheel-rail carrying devices along the sinking narrow rails, and transferring to the temporary tray area in the waiting transfer area until all of the stacked biological culture tray bodies are transferred;

starting the wheel-rail carrying devices again after the preset operation device completes preset operation on the stacked biological culture tray bodies by the tray reversing area, and starting from one of the tray body areas farthest from the waiting transfer area, from far to near, lifting the stacked biological culture tray bodies in the waiting transfer area sequentially by the wheel-rail carrying devices along the sinking narrow rails, and transferring to an original tray array area until all of stacked biological culture tray bodies are transferred;

or further comprising a reversal tray, wherein each of the stacked biological culture tray bodies comprises a body tray and a plurality of biological culture trays overlapped on the body tray, and a biological culture tray located at a bottommost is detachably connected with the body tray, the reversal tray and the body tray are capable of being used interchangeably, and the tray reversing area is arranged at at least one end of the temporary tray array area in the waiting transfer area, the circular moving method for stacked biological culture tray bodies on a ground by the reciprocating operation device comprises:

placing the reversal tray in the tray reversing area;

transferring all the stacked biological culture tray bodies in the preset tray array area to the temporary tray array area;

moving the reciprocating operation device to a temporary tray array area adjacent to the tray reversing area and corresponding to one of the stacked biological culture tray bodies;

starting a performing mechanism of the reciprocating operation device, sequentially performing preset operation on each of the biological culture trays in one of the stacked biological culture tray bodies from top to bottom, and sequentially placing each of biological culture trays of completing preset operation on the reversal tray in the tray reversing area from bottom to top, so that a body tray of stacked biological culture tray body of completing preset operation becomes a new reversal tray, a corresponding area becomes a new tray reversing area, and an original tray reversing area becomes a part of the temporary tray array area;

then moving the reciprocating operation device to a temporary tray array area adjacent to the new tray reversing area, and corresponding to a stacked biological culture tray body waiting for preset operation;

starting a performing mechanism of the reciprocating operation device, sequentially performing preset operation on each of biological culture trays in one of the stacked biological culture tray bodies waiting for preset operation from top to bottom, and sequentially placing each of biological culture trays of completing the preset operation on a new reversal tray on a new tray reversing area from bottom to top, so that the body tray of each of the stacked biological culture tray bodies of completing preset operation becomes into another new reversal tray, a corresponding area becomes another new tray reversing area, and an original new tray reversing area becomes a part of the temporary tray array area;

and so on, until all stacked biological culture tray bodies waiting for preset operation in the temporary tray array area complete preset operation, a body tray of a stacked biological culture tray body of completing the preset operation finally becomes a last new reversal tray, and a corresponding area becomes a last new tray reversing area; and sequentially transferring each of the stacked biological culture tray bodies of completing preset operation in the temporary tray array area to the original tray array area;

or further comprising a reversal tray, wherein each of the stacked biological culture tray bodies comprises a body tray and a plurality of biological culture trays overlapped on the body tray, and a biological culture tray located at a bottommost is detachably connected with the body tray, the reversal tray and the body tray are capable of being used interchangeably, and the tray reversing area is arranged in a middle of the temporary tray array area in the waiting transfer area, and is located near the tray array area of being preset to wait for preset operation, the circular moving method for stacked biological culture tray bodies on a ground by the reciprocating operation device comprises:

firstly transferring a part of stacked biological culture tray bodies in the preset tray array area to the temporary tray array area on one side of the tray array area in the waiting transfer area, then transferring another part of stacked biological culture tray bodies in the preset tray array area to the temporary tray array area on an other side of the tray array area in the waiting transfer area, and setting the tray reversing area at a position near an intersection of the tray array area and the waiting transfer area;

placing the reversal tray in the tray reversing area;

moving the reciprocating operation device to a temporary tray array area adjacent to the tray reversing area at one side of the tray reversing area and corresponding to one of the stacked biological culture tray bodies;

starting a performing mechanism of the reciprocating operation device, sequentially performing preset operation on each of biological culture trays in one of the stacked biological culture tray bodies waiting for preset operation from top to bottom, and sequentially placing each of biological culture trays of completing preset operation on a reversal tray on a tray reversing area from bottom to top, so that the body tray of each of the stacked biological culture tray bodies of completing preset operation becomes into another new reversal tray, a corresponding area becomes another new tray reversing area, and an original tray reversing area becomes a part of the temporary tray array area;

then moving the reciprocating operation device to a temporary tray array area adjacent to the new tray reversing area, and corresponding to one of the stacked biological culture tray bodies waiting for preset operation;

starting a performing mechanism of the reciprocating operation device, sequentially performing preset operation on each of the biological culture trays in one of the stacked biological culture disc bodies waiting for preset operation from top to bottom, and sequentially placing each of the biological culture trays of completing preset operation on a new reversal tray on a new tray reversing area from bottom to top, so that the body tray of each of the stacked biological culture disc bodies of completing preset operation becomes another new reversal tray, a corresponding area becomes another new tray reversing area, and an original new tray reversing area becomes a part of the temporary tray array area;

and so on, until all the stacked biological culture tray bodies waiting for preset operation in the temporary tray array area at one side of the tray reversing area completes preset operation, the body tray of one of the stacked biological culture tray bodies of completing the preset operation finally becomes another new reversal tray, and corresponding area becomes another new tray reversing area;

sequentially transferring each of the stacked biological culture tray bodies of having completed preset operation in the temporary tray array area to an original tray array area;

transferring another new reversal tray to an opposite end of a temporary tray array area on an other side;

similarly, moving the reciprocating operation device to the temporary tray array area on the other side and corresponding to one of the stacked biological culture tray bodies adjacent to another new reversal tray;

repeating above operation flow until remaining stacked biological culture tray bodies complete preset operation and sequentially transferring to an original tray array area.

7. The circular moving method for stacked biological culture trays on a ground according to claim 6, wherein the tray array area and the waiting transfer area are provided with navigation signals of being mutually connected and used in cooperation, and the navigation signals are used in cooperation with carrying robots, and the universal wheel tray is applied force by each of the carrying robots, and the circular moving method for stacked biological culture trays on a ground comprises:

starting the carrying robots when preset operation is necessary to performed on the stacked biological culture tray bodies in the preset tray array area, and starting from a tray body area nearest from the waiting transfer area, lifting or semi-lifting the stacked biological culture tray bodies in the tray array areas one by one from near to far by using the carrying robots according to the navigation signals, and transferring out of the tray array areas in the first direction, and then transferring to the waiting transfer area in the second direction and sequentially placing in the temporary tray array area until all of the stacked biological culture tray bodies are transferred;

staring the carrying robots again after the preset operation device completes the preset operation on the stacked biological culture tray bodies by the tray reversing area, and starting from a tray body area farthest from the waiting transfer area, lifting or semi-lifting the stacked biological culture tray bodies in the waiting transfer area one by one from far to near by using the carrying robots according to the navigation signals, and transferring out of the tray array areas in the second direction, and then transferring to the waiting transfer area in the second direction and transferring to an original tray array area along the first direction until all of the stacked biological culture tray bodies are transferred.

8. The circular moving method for stacked biological culture trays on a ground according to claim 6, wherein a first connecting mechanism and a second connecting mechanism for chain traction are arrange at intervals at a bottom of the universal wheel tray, sinking slits of being low than the ground are arranged in the tray array areas along the first direction and in the waiting transfer area along the second direction, the sinking slits are used in cooperation with universal wheels of the universal wheel tray, the universal wheel tray is capable of spanning the sinking slits, and a first chain sprocket assembly is arranged in a sinking slit of the tray array areas, the first chain sprocket assembly is provided with a first matching structure matched with the first connecting mechanism, and the first connecting mechanism and the first matching structure are capable of being connected or separated according to instructions; a second chain sprocket assembly is arranged in a sinking slit of the waiting transfer area, and the second chain sprocket assembly is provided with a second matching structure matched with the second connecting mechanism, and the second connecting mechanism and the second matching structure are capable of being connected or separated according to instructions; the circular moving method for stacked biological culture trays on a ground comprises:

firstly starting the first chain sprocket assembly to drive the first matching structure to rotate in a direction of the waiting transfer area when preset operation is necessary to performed on the stacked biological culture tray bodies in the preset tray array area, firstly connecting the first connecting mechanism of a universal wheel tray closest to the waiting transfer area with the first matching structure in an order from near to far, and continuously rotating the first chain sprocket assembly in a direction of the waiting transfer area, until the second connecting mechanism of the universal wheel tray moves to a position corresponding to the second chain sprocket assembly in the waiting transfer area, so that the first matching structure is separated from the first connecting mechanism, starting the second chain sprocket assembly to drive the second matching structure to approach the second connecting mechanism, so that the second matching structure is connected with the second connecting mechanism, and starting the second chain sprocket assembly to drive the universal wheel tray to move to a predetermined position in the temporary tray array area, so that the second matching structure and the second connecting mechanism are separated;

and so on, until all the stacked biological culture tray bodies in the tray array areas are transferred to the temporary tray array area in the waiting transfer area one by one;

after the preset operation device completes preset operation on the stacked biological culture tray bodies by the tray reversing area, firstly starting the second chain sprocket assembly in an order from near to far, so that a second connecting mechanism of a universal wheel tray closest to the tray array area is connected with a second matching structure, and continuously rotating the second chain sprocket assembly in a direction of the tray array area until the first connecting mechanism of the universal wheel tray moves a position corresponding to the first chain sprocket assembly, so that the second matching structure is separated from the second connecting mechanism, then starting the first chain sprocket assembly, so that first matching structure is connected with the first connecting mechanism, and starting the first chain sprocket assembly to drive the universal wheel tray to transfer to a predetermined position in each of the tray array areas, so as to separate the first matching structure from the first connecting mechanism;

and so on, until all the stacked biological culture tray bodies in the waiting transfer area are transferred to the tray array areas one by one.

9. A pasture plant adopting the circulating operation method of the stacked biological culture trays on a ground according to claim 6, and operating on a circulating moving layout structure of the stacked biological culture trays on a ground;

wherein the circular moving layout structure of stacked biological culture trays on a ground comprises display areas, a waiting transfer area and an operation area, wherein each of the display areas comprises a plurality of tray array areas, each of the tray array areas comprises a plurality of tray body areas, and the plurality of tray body areas are arranged in a single row along a first direction, and one of stacked biological culture tray bodies is correspondingly placed in each of the tray body areas in each of the tray array areas, and the stacked biological culture tray bodies are used for cultivating preset organisms, vertical projection areas of each of stacked biological culture tray bodies in each of the tray array areas on a ground are connected in a rectangular outline, each of the tray array areas is rectangular with long sides in the first direction, and a plurality of the tray array areas are arranged as the display areas along a second direction, and the first direction and the second direction are vertically arranged;

the waiting transfer area comprises a temporary tray array area and at least one tray reversing area, wherein the temporary tray array area is used for temporarily accommodating all the stacked biological culture tray bodies in at least one of the tray array areas, and the tray reversing area is used for temporarily accommodating at least one of the stacked biological culture tray bodies; the tray reversing area is arranged at an end of the temporary tray array area and communicates with the temporary tray array area from one side, or, the tray reversing area is arranged in a middle of the temporary tray reversing area to divide the temporary tray array area into two sections and communicate with the temporary tray array area from two sides; the temporary tray array area is used in cooperation with the tray reversing area, so as to perform preset operation on each of the stacked biological culture tray bodies; vertical projection areas of all the stacked biological culture tray bodies accommodated in the waiting transfer area on the ground are connected in a rectangular outline, the waiting transfer area is rectangular with long sides in the second direction, and a length of the waiting transfer area is greater than a sum of a length of at least one of the tray array areas and a length of the tray reversing area; a long side of the waiting transfer area corresponds to a short side of each of the tray array areas in each of the display areas, a width of the waiting transfer area is greater than or equal to a maximum side length of each of the tray body areas, the waiting transfer area is interconnected with each of the tray array areas in each of the display areas, and all the stacked biological culture tray bodies in each of the tray array areas perform barrier-free sequential circular movement between the tray array areas and the waiting transfer area in a full-in and full-out manner;

the waiting transfer area is connected with the operation area for use;

the operation area is used for arranging a reciprocating operation device of being capable of moving back and forth, and the reciprocating operation device moves back and forth on two long sides of the waiting transfer area in the second direction; vertical projection areas of the reciprocating operation device on the ground are connected in a rectangular outline during reciprocating movement; the operation area covers the waiting transfer area; a width of the operation area is greater than a width of the waiting transfer area; a length of the operation area is greater than or equal to a length of the waiting transfer area, so that the reciprocating operation device is capable of riding across the waiting transfer area for reciprocating movement, and during reciprocating movement, preset operation is performed on the stacked biological culture tray bodies in any position of the temporary tray array area by the tray reversing area, and a barrier-free movement of the stacked biological culture tray bodies between each of the tray array areas and the waiting transfer area is not hindered; or, the operation area is used for arranging reciprocating operation device of being capable of moving reciprocally, and the reciprocating operation device moves reciprocally along a long side of the waiting transfer area in the second direction, and vertical projection areas of the reciprocating operation device on the ground during reciprocating movement are connected in a rectangular outline, and the operation area is adjacent to the waiting transfer area, and a length of the operation area is greater than or equal to a length of the waiting transfer area, so that the reciprocating operation device is capable of moving reciprocally along a side of the waiting transfer area, and during reciprocating movement, preset operation is performed on the stacked biological culture tray bodies in any position of the temporary tray array area by the tray reversing area, and a barrier-free movement of the stacked biological culture tray bodies between the tray array areas and the waiting transfer area is not hindered;

one of the display areas is configured in one waiting transfer area and one operation area, and one of the display areas is arranged on one side of one long side of the waiting transfer area and the operation area; or, two the display areas are configured in one waiting transfer area and one operation area, and one of the display areas is respectively arranged on each side of two long sides of the waiting transfer area and the operation area, wherein one waiting transfer area and one operation area is provided with one display area, and one side of the long sides of the waiting transfer area and the operation area is provided with the display area, the plant further comprises a biological harvesting and transferring parking space, a biological harvesting and transferring conveyor belt, a biological species sowing and supplying conveyor belt, a biological species processing facility and a biological cultivation water supplying facility, wherein the biological harvesting and transferring parking space is arranged at preset ends of the waiting transfer area and the operation area in the second direction, and the biological harvesting and transferring conveyor belt is arranged corresponding to the operation area and arranged outside the operation area, and is used for receiving pasture products harvested from the stacked biological culture tray bodies by the reciprocating operation device and transferring to the biological harvesting and transferring parking space so as to be quickly loaded and transported away, wherein the biological species processing facility is arranged outside one side of the display area away from the biological harvesting and transferring parking space, and the biological species sowing and feeding conveyor belt is arranged corresponding to the operation area and arranged outside the operation area, the biological species sowing and supplying conveyor belt is arranged in parallel with the biological species harvesting and transferring conveyor belt and is located at one side or below the biological species harvesting and transferring conveyor belt; one end of the biological species sowing and supplying conveyor belt reaches the biological species harvesting and transferring parking space, and an other end reaches the biological species processing facility for receiving pasture seeds from biological harvesting and transferring parking space, and transferring the seeds to the biological species processing facility; and the biological cultivation water supplying facility is arranged outside one side of the display area away from the waiting transfer area, and is used for supplying the stacked biological culture trays in each of the tray array areas with water required for cultivating pasture.

* * * * *